US006501822B2

(12) United States Patent
Roder

(10) Patent No.: US 6,501,822 B2
(45) Date of Patent: *Dec. 31, 2002

(54) Z-AXIS ELIMINATION IN AN X-RAY LAMINOGRAPHY SYSTEM USING IMAGE MAGNIFICATION FOR Z PLANE ADJUSTMENT

(75) Inventor: Paul A. Roder, San Diego, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/032,240

(22) Filed: Dec. 21, 2001

(65) Prior Publication Data

US 2002/0080913 A1 Jun. 27, 2002

Related U.S. Application Data

(63) Continuation of application No. 09/652,255, filed on Aug. 30, 2000, now Pat. No. 6,373,917.

(51) Int. Cl.[7] .................................................. G01N 23/18
(52) U.S. Cl. .............................. 378/22; 378/25; 378/58; 382/147; 382/149
(58) Field of Search .............................. 378/22, 58, 25, 378/21, 24, 62, 207; 382/147, 149, 145, 150

(56) References Cited

U.S. PATENT DOCUMENTS

| 4,809,308 | A | * | 2/1989 | Adams et al. | ................. | 378/58 |
| 4,852,131 | A | * | 7/1989 | Armistead | ..................... | 378/17 |
| 4,926,452 | A | * | 5/1990 | Baker et al. | ............... | 250/358.1 |
| 5,081,656 | A | * | 1/1992 | Baker et al. | ................... | 348/87 |
| 5,097,492 | A | * | 3/1992 | Baker et al. | ................ | 378/205 |
| 5,199,054 | A | * | 3/1993 | Adams et al. | .............. | 378/124 |
| 5,259,012 | A | * | 11/1993 | Baker et al. | ................ | 378/137 |
| 5,291,535 | A | * | 3/1994 | Baker et al. | ................ | 378/207 |
| 5,500,886 | A | * | 3/1996 | Duff | .......................... | 378/207 |
| 5,561,696 | A | * | 10/1996 | Adams et al. | ................ | 378/58 |
| 5,583,904 | A | * | 12/1996 | Adams | ........................ | 378/22 |
| 5,592,562 | A | * | 1/1997 | Rooks | ......................... | 29/830 |
| 5,594,770 | A | * | 1/1997 | Bowles et al. | ................ | 378/4 |
| 5,621,811 | A | * | 4/1997 | Roder et al. | ................ | 348/126 |
| 5,687,209 | A | * | 11/1997 | Adams | ........................ | 378/22 |
| 6,373,917 | B1 | * | 4/2002 | Roder | ......................... | 378/22 |

* cited by examiner

Primary Examiner—Drew A. Dunn

(57) ABSTRACT

Systems and methods for analyzing for images in an x-ray inspection system are provided. One embodiment is a system for analyzing images in an x-ray inspection system. Briefly described, one such system comprises: a means for receiving an image of an object that is generated by an x-ray inspection system, the image of the object having a first field of view (FOV); a means for determining whether the first FOV associated with the image of the object matches a reference FOV corresponding to design data that models the object being inspected by the x-ray inspection system; and a means for modifying the design data based on the difference between the first FOV and the reference FOV.

30 Claims, 16 Drawing Sheets

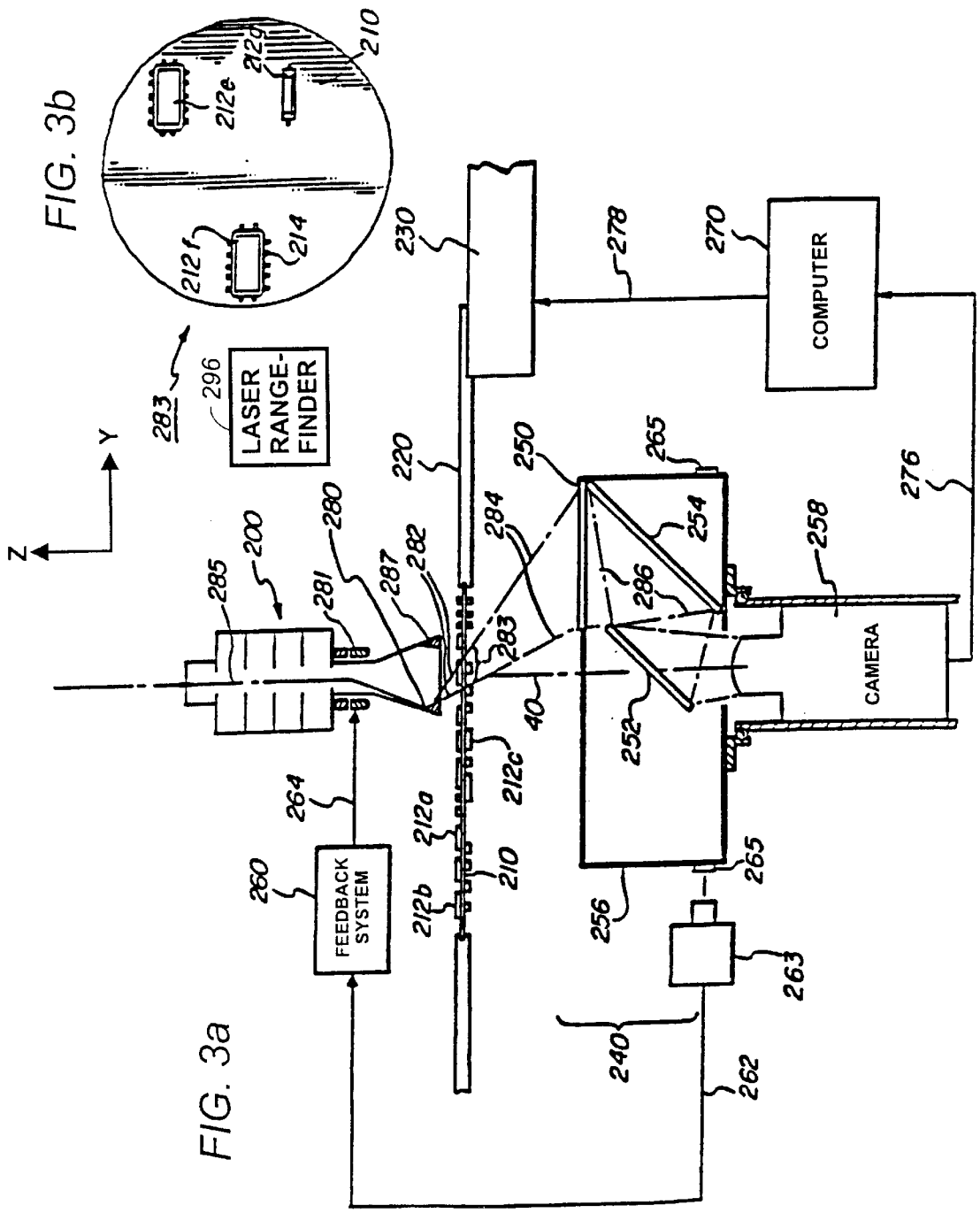

Z-AXIS ELIMINATION IN AN X-RAY LAMINOGRAPHY SYSTEM USING IMAGE MAGNIFICATION FOR Z PLANE ADJUSTMENT

CROSS-REFERENCE TO RELATED APPLICATION

This application is a continuation of copending U.S. utility application entitled, "Z-Axis Elimination in an X-Ray Laminography System Using Image Magnification for Z Plane Adjustment," having Ser. No. 09/652,255 and filed Aug. 30, 2000, now U.S. Pat. No. 6,373,917 which is entirely incorporated herein by reference.

FIELD OF THE INVENTION

The invention relates generally to the rapid, high resolution inspection of circuit boards using a computerized laminography system, and in particular, to systems which use electronic means to adjust the Z-axis location of the inspection site with respect to the circuit board.

BACKGROUND OF THE INVENTION

Rapid and precise quality control inspections of the soldering and assembly of electronic devices have become priority items in the electronics manufacturing industry. The reduced size of components and solder connections, the resulting increased density of components on circuit boards and the advent of surface mount technology (SMT), which places solder connections underneath device packages where they are hidden from view, have made rapid and precise inspections of electronic devices and the electrical connections between devices very difficult to perform in a manufacturing environment.

Many existing inspection systems for electronic devices and connections make use of penetrating radiation to form images which exhibit features representative of the internal structure of the devices and connections. These systems often utilize conventional radiographic techniques wherein the penetrating radiation comprises X-rays. Medical X-ray pictures of various parts of the human body, e.g., the chest, arms, legs, spine, etc., are perhaps the most familiar examples of conventional radiographic images. The images or pictures formed represent the X-ray shadow cast by an object being inspected when it is illuminated by a beam of X-rays. The X-ray shadow is detected and recorded by an X-ray sensitive material such as film or other suitable means.

The appearance of the X-ray shadow or radiograph is determined not only by the internal structural characteristics of the object, but also by the direction from which the incident X-rays strike the object. Therefore, a complete interpretation and analysis of X-ray shadow images, whether performed visually by a person or numerically by a computer, often requires that certain assumptions be made regarding the characteristics of the object and its orientation with respect to the X-ray beam. For example, it is often necessary to make specific assumptions regarding the shape, internal structure, etc. of the object and the direction of the incident X-rays upon the object. Based on these assumptions, features of the X-ray image may be analyzed to determine the location, size, shape, etc., of the corresponding structural characteristic of the object, e.g., a defect in a solder connection, which produced the image feature. These assumptions often create ambiguities which degrade the reliability of the interpretation of the images and the decisions based upon the analysis of the X-ray shadow images. One of the primary ambiguities resulting from the use of such assumptions in the analysis of conventional radiographs is that small variations of a structural characteristic within an object, such as the shape, density and size of a defect within a solder connection, are often masked by the overshadowing mass of the solder connection itself as well as by neighboring solder connections, electronic devices, circuit boards and other objects. Since the overshadowing mass and neighboring objects are usually different for each solder joint, it is extremely cumbersome and often nearly impossible to make enough assumptions to precisely determine shapes, sizes and locations of solder defects within individual solder joints.

In an attempt to compensate for these shortcomings, some systems incorporate the capability of viewing the object from a plurality of angles. One such system is described in U.S. Pat. No. 4,809,308 entitled "METHOD & APPARATUS FOR PERFORMING AUTOMATED CIRCUIT BOARD SOLDER QUALITY INSPECTIONS", issued to Adams et al. The additional views enable these systems to partially resolve the ambiguities present in the X-ray shadow projection images. However, utilization of multiple viewing angles necessitates a complicated mechanical handling system, often requiring as many as five independent, non-orthogonal axes of motion. This degree of mechanical complication leads to increased expense, increased size and weight, longer inspection times, reduced throughput, impaired positioning precision due to the mechanical complications, and calibration and computer control complications due to the non-orthogonality of the axes of motion.

Many of the problems associated with the conventional radiography techniques discussed above may be alleviated by producing cross-sectional images of the object being inspected. Tomographic techniques such as laminography and computed tomography (CT) have been used in medical applications to produce cross-sectional or body section images. In medical applications, these techniques have met with widespread success, largely because relatively low resolution on the order of one or two millimeters (0.0425 to 0.08 inches) is satisfactory and because speed and throughput requirements are not as severe as the corresponding industrial requirements.

In the case of electronics inspection, and more particularly, for inspection of electrical connections such as solder joints, image resolution on the order of several micrometers, for example, 20 micrometers (0.0008 inches) is preferred. Furthermore, an industrial solder joint inspection system must generate multiple images per second in order to be practical for use on an industrial production line. Laminography systems which are capable of achieving the speed and accuracy requirements necessary for electronics inspection are described in the following patents: 1) U.S. Pat. No. 4,926,452 entitled "AUTOMATED LAMINOGRAPHY SYSTEM FOR INSPECTION OF ELECTRONICS", issued t0 Baker et al.; 2) U.S. Pat. No. 5,097,492 entitled "AUTOMATED LAMINOGRAPHY SYSTEM FOR INSPECTION OF ELECTRONICS", issued to Baker et al.; 3) U.S. Pat. No. 5,081,656 entitled "AUTOMATED LAMINOGRAPHY SYSTEM FOR INSPECTION OF ELECTRONICS", issued to Baker et al.; 4) U.S. Pat. No. 5,291,535 entitled "METHOD AND APPARATUS FOR DETECTING EXCESS/INSUFFICIENT SOLDER DEFECTS", issued to Baker et al.; 5) U.S. Pat. No. 5,621,811 entitled "LEARNING METHOD AND APPARATUS FOR DETECTING AND CONTROLLING SOLDER DEFECTS", issued to Roder et al.; 6) U.S. Pat. No. 5,561, 696 "METHOD & APPARATUS FOR INSPECTING ELECTRICAL CONNECTIONS", issued to Adams et al.; 7) U.S. Pat. No. 55,199,054 entitled "METHOD AND APPARATUS FOR HIGH RESOLUTION INSPECTION OF ELECTRONIC ITEMS", issued to Adams et al.; 8) U.S. Pat. No. 5,259,012 entitled "LAMINOGRAPHY SYSTEM AND METHOD WITH ELECTROMAGNETICALLY DIRECTED MULTIPATH RADIATION SOURCE", issued to Baker et al.; 9) U.S. Pat. No. 5,583,904 entitled "CONTINUOUS LINEAR SCAN LAMINOGRAPHY SYSTEM AND METHOD", issued to Adams; and 10) U.S. Pat. No. 5,687,209 entitled "AUTOMATIC WARP COMPENSATION FOR LAMINOGRAPHIC CIRCUIT BOARD INSPECTION", issued to Adams. The entirety of each of the above referenced patents is hereby incorporated herein by reference.

Several of the above referenced patents disclose devices and methods for the generation of cross-sectional images of test objects at a fixed or selectable cross-sectional image focal plane. In these systems, an X-ray source system and an X-Ray detector system are separated in the Z-axis direction by a fixed distance and the cross-sectional image focal plane is located at a predetermined specific position on the Z-axis which is intermediate the Z-axis locations of the X-ray source system and the X-ray detector system. The X-ray detector system collects data from which a cross-sectional image of features in the test object, located at the cross-sectional image focal plane, can be formed. In systems having a fixed cross-sectional image focal plane, it is necessary to postulate that the features desired to be imaged are located in the fixed cross-sectional image focal plane at the predetermined specific position along the Z-axis. Thus, in these systems, it is essential that the positions of the fixed cross-sectional image focal plane and the plane with respect to the object which is desired to be imaged, be configured to coincide at the same position along the Z-axis. If this condition is not met, then the desired image of the selected feature of the test object will not be acquired. Instead, a cross-sectional image of a plane with respect to the test object which is either above or below the plane which includes the selected feature will be acquired. Thus, mechanical motion of the test object along the Z-axis is often used to position the desired plane with respect to the test object which is to be imaged at the position of the fixed cross-sectional image focal plane of the inspection system.

Since the laminographic image area (e.g., 2–3 cm$^2$) of a typical laminography system is substantially smaller than the area of a typical circuit board (e.g., 150–1,500 cm$^2$), a complete inspection of a circuit board includes multiple laminographic images, which, if pieced together would form an image of the entire circuit board or selected regions of the circuit board. Thus, in addition to having a Z-axis mechanical positioning system for placing the test object (circuit board) at a specific location along the Z-axis, a typical high resolution laminography system also includes X-axis and Y-axis mechanical positioning systems for placing the test object at specific locations along the X and Y axes. This is frequently achieved by supporting the test object on a mechanical handling system, such as an X,Y,Z positioning table. The table is then moved to bring the desired regions of the test object into the laminographic image area of the laminography system. Movement in the X and Y directions locates the region of the test object to be examined, while movement in the Z direction moves the test object up and down to select the plane with respect to the test object where the cross sectional image is to be taken. As used throughout this document, the phrase "board view" will be used to refer to the laminographic image of a particular region or area of a circuit board identified by a specific X,Y coordinate of the circuit board. Thus, each "board view" includes only a portion of the circuit board.

Many inspections require that some of the board views include multiple images at different Z-axis levels of the circuit board. This may be accomplished by physically moving the circuit board up or down in the Z-axis direction using the X,Y,Z mechanical positioning table. However, this additional mechanical motion along the Z-axis direction can also lead to increased expense, increased size and weight, longer inspection times, reduced throughput, reduced image resolution and accuracy due to mechanical vibrations and impaired Z-axis positioning precision due to mechanical complications.

An alternative to mechanical Z-axis positioning is disclosed in U.S. Pat. No. 5,259,012 entitled "LAMINOGRAPHY SYSTEM AND METHOD WITH ELECTROMAGNETICALLY DIRECTED MULTIPATH RADIATION SOURCE", issued to Baker et al. This patent describes a laminography system which electronically shifts the Z-axis location of the image plane with respect to the test object. In this device, the test object is interposed between a rotating X-Ray source and a synchronized rotating X-ray detector. A focal plane with respect to the test object is imaged onto the detector so that a cross-sectional image of a layer of the test object which coincides with the image focal plane is produced. The X-ray source is produced by deflecting an electron beam onto a target anode. The target anode emits X-ray radiation where the electrons are incident upon the target anode. The electron beam is produced by an electron gun which includes X and Y deflection coils for deflecting the electron beam in the X and Y directions. The X and Y deflection coils cause the X-ray source to rotate in a circular trace path. The voltages applied to the X and Y deflection coils are adjusted to change the radius of the circular trace path on the target anode resulting in a change in the Z-axis location of the image plane with respect to the test object. A characteristic of this type of electronic Z-axis positioning system is that images produced at different Z-axis positions have different magnification factors. The different magnification factors of the images complicates the analysis of the multiple images acquired during a complete inspection of the circuit board.

In summary, the magnification of multiple board views at different Z levels is not changed when using systems of the type previously described wherein the X-ray source and detector are fixed at specific locations along the Z-axis and the circuit board is moved in the Z-axis direction to obtain laminographic images at the different Z levels of the circuit board. Alternatively, the magnification of different Z level board views does change with each change in Z level when using the previously described systems which electronically change the radius of the X-Ray source to obtain laminographic images at different Z levels of the circuit board. The different magnifications for different Z level board views in these systems presents difficulties in analyzing the images thus obtained.

The present invention provides improvements which address the above listed specific problems. The present invention advantageously includes ease of use and improved accuracy of Z elevation determination, resulting in an improved technique for producing high resolution cross sectional images of electrical connections.

SUMMARY OF THE INVENTION

The present invention comprises an improved computerized laminography system which accurately compensates for variable magnifications of different Z level board views in an efficient manner. This feature makes it feasible to eliminate the Z-axis mechanical motion of the circuit board along the Z-axis direction. Elimination of the Z-axis mechanical motion improves speed of the inspection as well as reliability of the inspection system.

As used throughout this document, the phrase "field of view" or "FOV" will be used to refer to the size of a particular region or area of a circuit board which is included in a laminographic image of that particular region or area of the circuit board. For example, one particular configuration of the present invention has two preset magnification factors. A first magnification factor of 4.75 has a FOV of 0.8 inch×0.8 inch and an image size of 3.8 inches×3.8 inches. Thus, a board view at a particular x,y location of the circuit board at a magnification of 4.75 refers to a 3.8 inches×3.8 inches image of a 0.8 inch×0.8 inch region of the circuit board centered at location x,y on the circuit board. A second magnification factor of 19 has a FOV of 0.2 inch×0.2 inch and an image size of 3.8 inches×3.8 inches. Thus, a board view at a particular x,y location of the circuit board at a magnification of 19 refers to a 3.8 inches×3.8 inches image of a 0.2 inch×0.2 inch region of the circuit board centered at location x,y on the circuit board. Thus, four board views at the magnification of 19, each board view having a FOV of 0.2 inch×0.2 inch, are required to image the single corresponding board view at the magnification of 4.75, each board view having a FOV of 0.8 inch×0.8 inch. In terms of FOV, the FOV of the system operating at a magnification factor of 4.75 is 4 times larger than the FOV of the system operating at a magnification factor of 19.

As described above, in addition to changing the magnification of the image, another side effect of changing the Z-axis location of the image plane electronically as opposed to mechanically is that the field of view (FOV) for different Z-axis locations of the image plane also changes as the magnification changes. In systems having a fixed Z-axis location of the image plane, the magnification and FOV are not dependent on which Z-level of the circuit board is being imaged since different Z-levels of the circuit board are mechanically positioned at the same fixed Z-axis location of the image plane of the system.

There are several ways that this change in FOV with magnification can be accounted for and corrected in analyzing the images. In circuit board inspection systems, CAD data which describes the circuit board being inspected is utilized during the acquisition and analysis of the images of the circuit board. Thus, a first technique for compensating for variable image magnification factors and FOV's may be accomplished by magnifying or shrinking the acquired images to a "nominal" size ("nominal" being defined by a base FOV). Numerous algorithms for doing this are well documented in the technical literature. However, these techniques tend to be CPU intensive and may affect throughput of the system. A second and preferred technique for compensating for variable image magnification factors and FOV's may be accomplished more efficiently by using on-the-fly CAD data manipulation and on-the-fly FOV adjustments during the analysis of the images.

In a first aspect, the present invention is a device for inspecting electrical connections on a circuit board comprising: a source of X-rays which emits X-rays through the electrical connection from a plurality of positions centered about a first radius and a second radius; an X-ray detector system positioned to receive the X-rays produced by the source of X-rays which have penetrated the electrical connection, the X-ray detector system further comprising an output which emits data signals; an image memory which combines the detector data signals to form an image database which contains information sufficient to form a first cross-sectional image of a cutting plane of the electrical connection at a first image plane at a first Z-axis location corresponding to the first X-ray source radius and a second cross-sectional image of a cutting plane of the electrical connection at a second image plane at a second Z-axis location corresponding to the second X-ray source radius; and a processor which controls the acquisition and formation of the cross-sectional images and analyzes the cross-sectional images, the image processor further comprising: a storage area for storing CAD data which describes a first cross-sectional design of the electrical connection at the first image plane at the first Z-axis location and CAD data for a second cross-sectional design of the electrical connection at the second image plane at the second Z-axis location; and a CAD data calculator section which determines a variance between the first cross-sectional image at the first image plane and the second cross-sectional image at the second image plane and uses the variance to modify, on an as-needed basis, portions of the CAD data which describe said electrical connection at the second image plane at the second Z-axis location thereby generating modified CAD data for the second image plane which describes the electrical connection at the second image plane as represented by the second cross-sectional image. In some configurations, the first cross sectional image has a first field of view and the second cross sectional image has a second field of view and the variance between the first cross-sectional image and the second cross-sectional image is determined by comparing the second field of view to the first field of view. In some configurations, the first cross sectional image has a first magnification factor and the second cross sectional image has a second magnification factor and the variance between the first cross-sectional image and the second cross-sectional image is determined by comparing the second magnification factor to the first magnification factor. In some configurations, the source of X-rays comprises a plurality of X-ray sources. In some configurations, the X-ray detector system comprises a plurality of X-ray detectors. In some configurations, the processor further comprises an image section which produces the cross-sectional images of the electrical connection from the image database.

A second aspect of the present invention includes a method for analyzing laminographic images of an object at multiple Z-axis levels within the object comprising the steps of: determining a reference Z-axis position $Z_1$, corresponding to a first Z level in the object; acquiring a first cross sectional image of the object at the reference Z-axis position $Z_1$, which corresponds to the first Z level in the object and a second cross sectional image of the object at a second Z-axis position $Z_2$ which corresponds to a second Z level in the object; providing first Z level design data which describes the object and specific features within the object at the first Z level of the object and second Z level design data which describes the object and specific features within the object at the second Z level of the object; determining a variance factor which represents a difference between the first cross sectional image of the object at the first Z level and the second cross sectional image of the object at the second Z level; and modifying in real time or near real time, one or more portions of the second Z level design data with the variance factor while comparing the second cross sectional image of the object at the second Z level with the real time or near real time modified second Z level design data. In some implementations of the method, the first cross sectional image has a first field of view and the second cross sectional image has a second field of view and the variance factor which represents a difference between the first cross-sectional image and the second cross-sectional image is determined by comparing the second field of view to the first field of view. In some implementations of the method, the first cross sectional image has a first magnification factor and the second cross sectional image has a second magnification factor and the variance factor which represents a difference between the first cross-sectional image and the second cross-sectional image is determined by comparing the second magnification factor to the first magnification factor.

A third aspect of the present invention includes a method for inspecting an electrical connection on a circuit board comprising: determining a first Z-axis position $Z_1$, corresponding to a first Z level in the electrical connection; acquiring a first cross sectional image of the electrical connection at the first Z-axis position $Z_1$, which corresponds to the first Z level in the electrical connection and a second cross sectional image of the electrical connection at a second Z-axis position $Z_2$ which corresponds to a second Z level in the electrical connection, wherein the first cross sectional image has a first magnification factor and the second cross sectional image has a second magnification factor; providing first Z level design data which describes the electrical connection and specific design features within the electrical connection at the first Z level of the electrical connection and second Z level design data which describes the electrical connection and specific design features within the electrical connection at the second Z level of the electrical connection; comparing the first and second magnification factors to determine a first field of view correction factor; and modifying in real time or near real time, one or more portions of the second Z level design data with the first field of view correction factor while comparing the second cross sectional image of the electrical connection at the second Z level with the real time or near real time modified second Z level design data.

Some implementations of this method further comprise: providing third Z level design data which describes the electrical connection and specific design features within the electrical connection at a third Z level of the electrical connection; acquiring a third cross sectional image of the electrical connection at a third Z-axis position $Z_3$ which corresponds to the third Z level in the electrical connection wherein the third cross sectional image has a third magnification factor; comparing the first and third magnification factors to determine a second field of view correction factor; and modifying in real time or near real time, one or more portions of the third Z level design data with the second field of view correction factor while comparing the third cross sectional image of the electrical connection at the third Z level with the real time or near real time modified third Z level design data.

These and other characteristics of the present invention will become apparent through reference to the following detailed description of the preferred embodiments and accompanying drawings.

BRIEF DESCRIPTION OF THE DRAWINGS

FIG. 2e shows a conventional, two-dimensional X-ray projection image of the object in FIG. 2a.

FIG. 3a is a diagrammatic cross-sectional view of a circuit board inspection laminography system showing how the laminographic image is formed and viewed by a camera.

FIG. 3b shows a top view enlargement of an inspection region shown in FIG. 3a.

FIG. 3c is a perspective view of the circuit board inspection laminography system shown in FIG. 3a.

Figure 1:
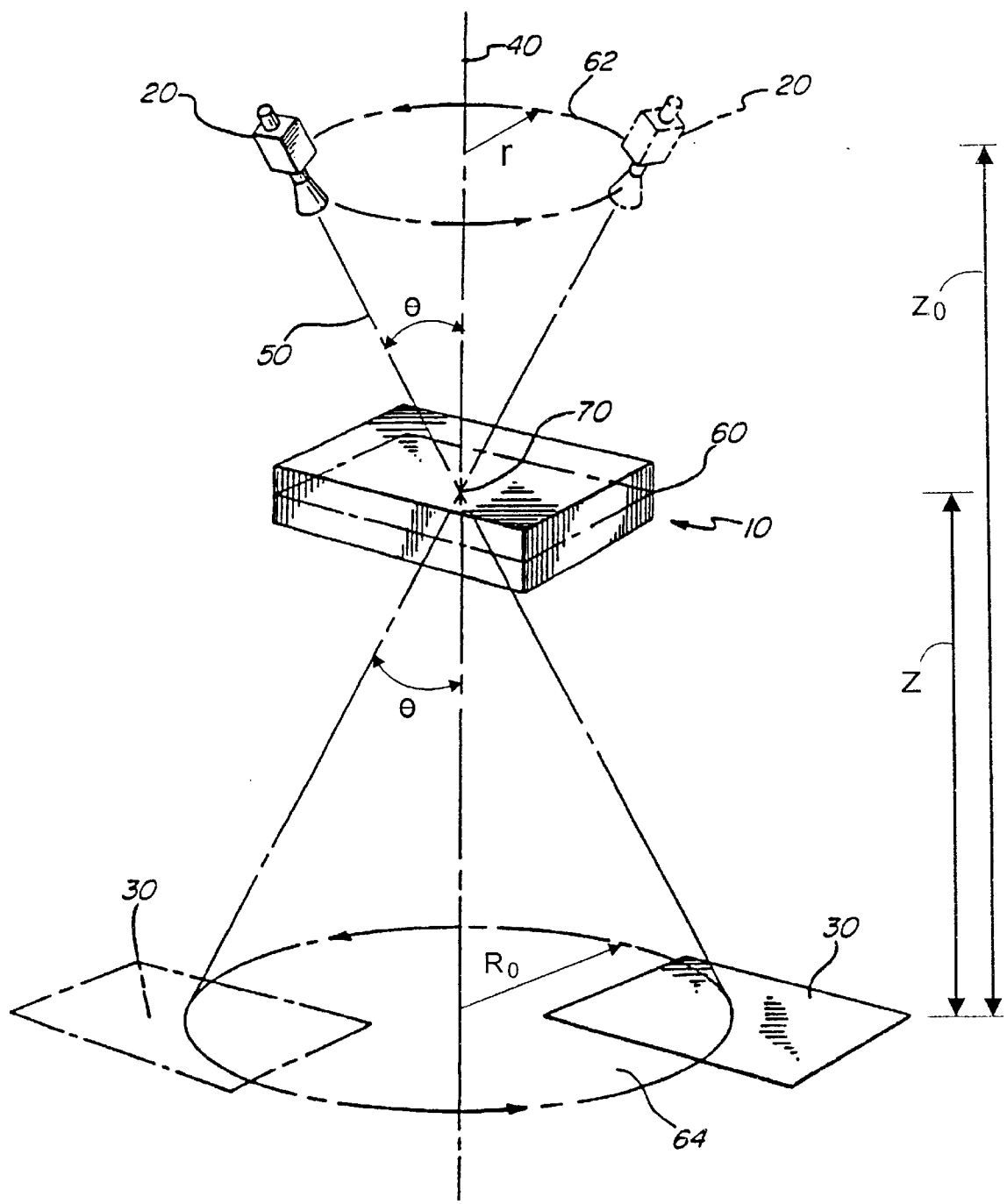
FIG. 1 is a schematic representation of a laminography system illustrating the principles of the technique.

REFERENCE NUMERALS IN DRAWINGS 10 object under inspection
20 source of X-rays
30 X-ray detector
40 common axis of rotation
50 central ray
52 X-ray projection
60 image plane in object 10
60a arrow image plane
60b circle image plane
60c cross image plane
62 plane of source of X-rays
64 plane of X-ray detecto
70 point of intersection
81 arrow test pattern
82 circle test pattern
83 cross test pattern
100 image of arrow 81
102 blurred region
100 image of circle 82
112 blurred region
120 image of cross 83
122 blurred region 130 image of arrow 81
132 image of circle 82
134 image of cross 83
200 X-ray tube
210 printed circuit board
212 electronic components
214 electrical connections
220 support fixture
230 positioning table
240 rotating X-ray detector
250 fluorescent screen
252 first mirror
254 second mirror
256 turntable
258 camera
260 feedback system
262 input connection
263 sensor
264 output connection
265 position encoder
270 computer
276 input line
278 output line
280 rotating source spot
281 deflection coils
282 X-rays
283 region of circuit board
284 X-rays
285 rotating electron beam
286 light
287 target anode
290 granite support table
292 load/unload port
294 operator station
296 laser range finder
310 laminography system
312 source of X-rays
314 object
315 analysis system
316 rotating X-ray detector
318 electron gun
320 electrodes
322 coils
324 target anode
330 electron beam
332 X-ray spot
334 X-rays
340 fluorescent screen
342 first mirror
344 second mirror
346 turntable
348 platform
349 granite table
350 axis
352 plane
356 camera
357 video terminal
360 focus coil
362 steering yoke/deflection coil
363 look up table (LUT)
410 first plane of object 414
412 second plane of object 414
414 object under inspection
416 cone of X-rays
418 cone of X-rays
420 image of cross 472
424 scan circle with radius R1
425 scan circle with radius R2
426 cone of X-rays
428 cone of X-rays
430 image of arrow 470
470 arrow test pattern
472 cross test pattern
550 target anode
560 X-rays
620 circuit board
640 Field of View (FOV)
720*cd* CAD data for test object 10 at Level 1
720*id* image data for test object 10 at Level 1
750*cd* CAD data for test object 10 at Level 2
750*id* image data for test object 10 at Level 2
780*cd* CAD data for test object 10 at Level 3
780*id* image data for test object 10 at Level 3
810 flow chart process block
820 flow chart process block
830 flow chart process block
840 flow chart process block
850 flow chart process block
860 flow chart process block

DETAILED DESCRIPTION OF THE PREFERRED EMBODIMENTS

As used throughout, the term "radiation" refers to electromagnetic radiation, including but not limited to the X-ray, gamma and ultraviolet portions of the electromagnetic radiation spectrum.

Cross-Sectional Image Formation

FIG. 1 shows a schematic representation of a typical laminographic geometry used with the present invention. An object 10 under examination, for example, a circuit board, is held in a stationary position with respect to a source of X-rays 20 and an X-ray detector 30. Synchronous rotation of the X-ray source 20 and detector 30 about a common axis 40 causes an X-ray image of the plane 60 with respect to the object 10 to be formed on the detector 30. The image plane 60 is substantially parallel to planes 62 and 64 defined by the rotation of the source 20 and detector 30, respectively. The image plane 60 is located at an intersection 70 of a central ray 50 from the X-ray source 20 and the common axis of rotation 40. This point of intersection 70 acts as a fulcrum for the central ray 50, thus causing an in-focus cross-sectional X-ray image of the object 10 at the plane 60 to be formed on detector 30 as the source and detector synchronously rotate about the intersection point 70. Structure with respect to the object 10 which lies outside of plane 60 forms a blurred X-ray image on detector 30.

In the laminographic geometry shown in FIG. 1, the axis of rotation of the radiation source 20 and the axis of rotation of the detector 30 are coaxial. However, it is not necessary that these axes of rotation of the radiation source and the detector 30 be coaxial. The conditions of laminography are satisfied and a cross-sectional image of the layer 60 will be produced as long as the planes of rotation 62 and 64 are mutually parallel, and the axes of rotation of the source and the detector are mutually parallel and fixed in relationship to each other. Coaxial alignment reduces the number of constraints upon the mechanical alignment of the apparatus.

FIGS. 2a–2e show laminographs produced by the above described laminographic technique. The object 10 shown in FIG. 2a has test patterns in the shape of an arrow 81, a circle 82 and cross 83 embedded within the object 10 in three different planes 60a, 60b and 60c, respectively.

Figure 2A:
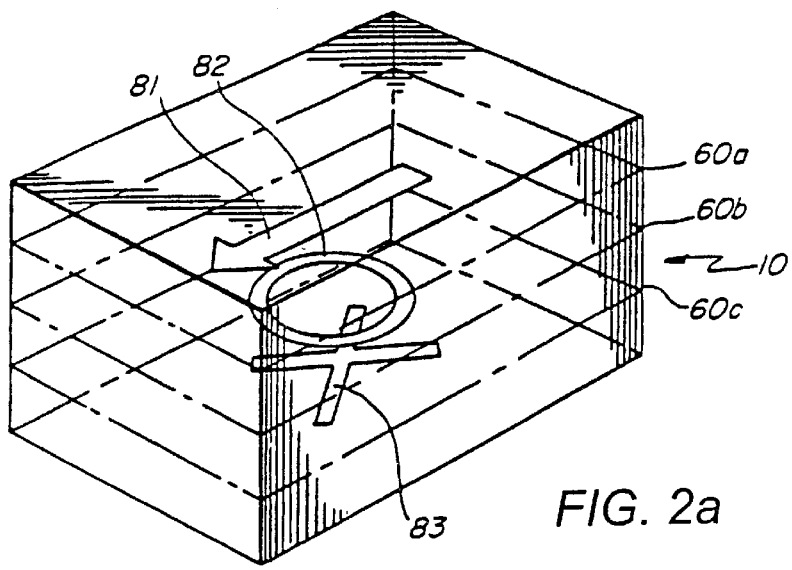
FIG. 2a shows an object having an arrow, a circle and a cross embedded in the object at three different planar locations.
Figure 2B:
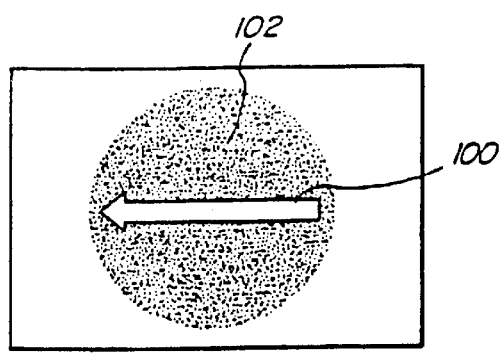
FIG. 2b shows a laminograph of the object in FIG. 2a focused on the plane containing the arrow.

FIG. 2b shows a typical laminograph of object 10 formed on detector 30 when the point of intersection 70 lies in plane 60a of FIG. 2a. An image 100 of arrow 81 is in sharp focus, while the images of other features within the object 10, such as the circle 82 and cross 83 form a blurred region 102 which does not greatly obscure the arrow image 100.

Figure 2D:
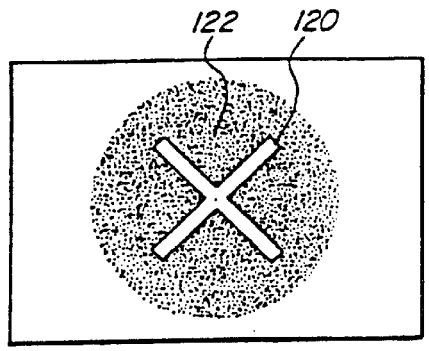
FIG. 2d shows a laminograph of the object in FIG. 2a focused on the plane containing the cross.
Figure 2C:
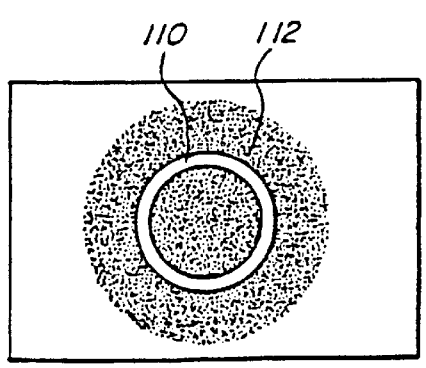
FIG. 2c shows a laminograph of the object in FIG. 2a focused on the plane containing the circle.

Similarly, when the point of intersection 70 lies in plane 60b, an image 110 of the circle 82 is in sharp focus as seen in FIG. 2c. The arrow 81 and cross 83 form a blurred region 112.

FIG. 2d shows a sharp image 120 formed of the cross 83 when the point of intersection 70 lies in plane 60c. The arrow 81 and circle 82 form blurred region 122.

Figure 2E:
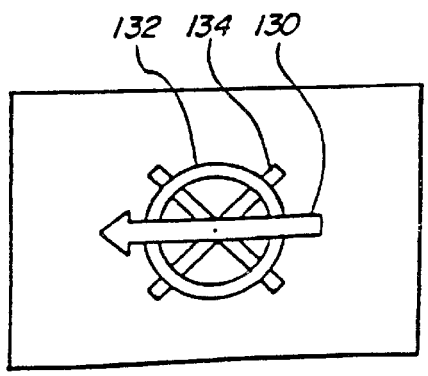

For comparison, FIG. 2e shows an X-ray shadow image of object 10 formed by conventional projection radiography techniques. This technique produces sharp images 130, 132 and 134 of the arrow 81, circle 82 and cross 83, respectively, which overlap one another. FIG. 2e vividly illustrates how multiple characteristics contained within the object 10 may create multiple overshadowing features in the X-ray image which obscure individual features of the image.

FIG. 3a illustrates a schematic diagram of a typical laminographic apparatus used with the present invention. In this configuration, an object under inspection is a printed circuit board 210 having multiple electronic components 212 mounted on the board 210 and electrically interconnected via electrical connections 214 (See FIG. 3b). Typically, the electrical connections 214 are formed of solder. However, various other techniques for making the electrical connections 214 are well know in the art and even though the invention will be described in terms of solder joints, it will be understood that other types of electrical connections 214 including, but not limited to, conductive epoxy, mechanical, tungsten and eutectic bonds may be inspected utilizing the invention. FIG. 3b, which is a top view enlargement of a region 283 of the circuit board 210, more clearly shows the components 212 and solder joints 214.

The laminographic apparatus acquires cross-sectional images of the solder joints 214 using the previously described laminographic method or other methods capable of producing equivalent cross-sectional images. The cross sectional images of the solder joints 214 are automatically evaluated to determine their quality. Based on the evaluation, a report of the solder joint quality is presented to the user.

The laminographic apparatus, as shown in FIG. 3a, comprises an X-ray tube 200 which is positioned adjacent printed circuit board 210. The circuit board 210 is supported by a fixture 220. The fixture 220 is attached to a positioning table 230 which is capable of moving the fixture 220 and board 210 along three mutually perpendicular axes, X, Y and Z. A rotating X-ray detector 240 comprising a fluorescent screen 250, a first mirror 252, a second mirror 254 and a turntable 256 is positioned adjacent the circuit board 210 on the side opposite the X-ray tube 200. A camera 258 is positioned opposite mirror 252 for viewing images reflected into the mirrors 252, 254 from fluorescent screen 250. A feedback system 260 has an input connection 262 from a sensor 263 which detects the angular position of the turntable 256 and an output connection 264 to X and Y deflection coils 281 on X-ray tube 200. A position encoder 265 is attached to turntable 256. The position sensor 263 is mounted adjacent encoder 265 in a fixed position relative to the axis of rotation 40. The camera 258 is connected to a computer 270 via an input line 276. The computer 270 includes the capability to perform high speed image analysis. An output line 278 from the computer 270 connects the computer to positioning table 230. A laser range finder 296 is positioned adjacent the circuit board 210 for creating a Z-map of the surface of the circuit board 210.

Figure 3C:
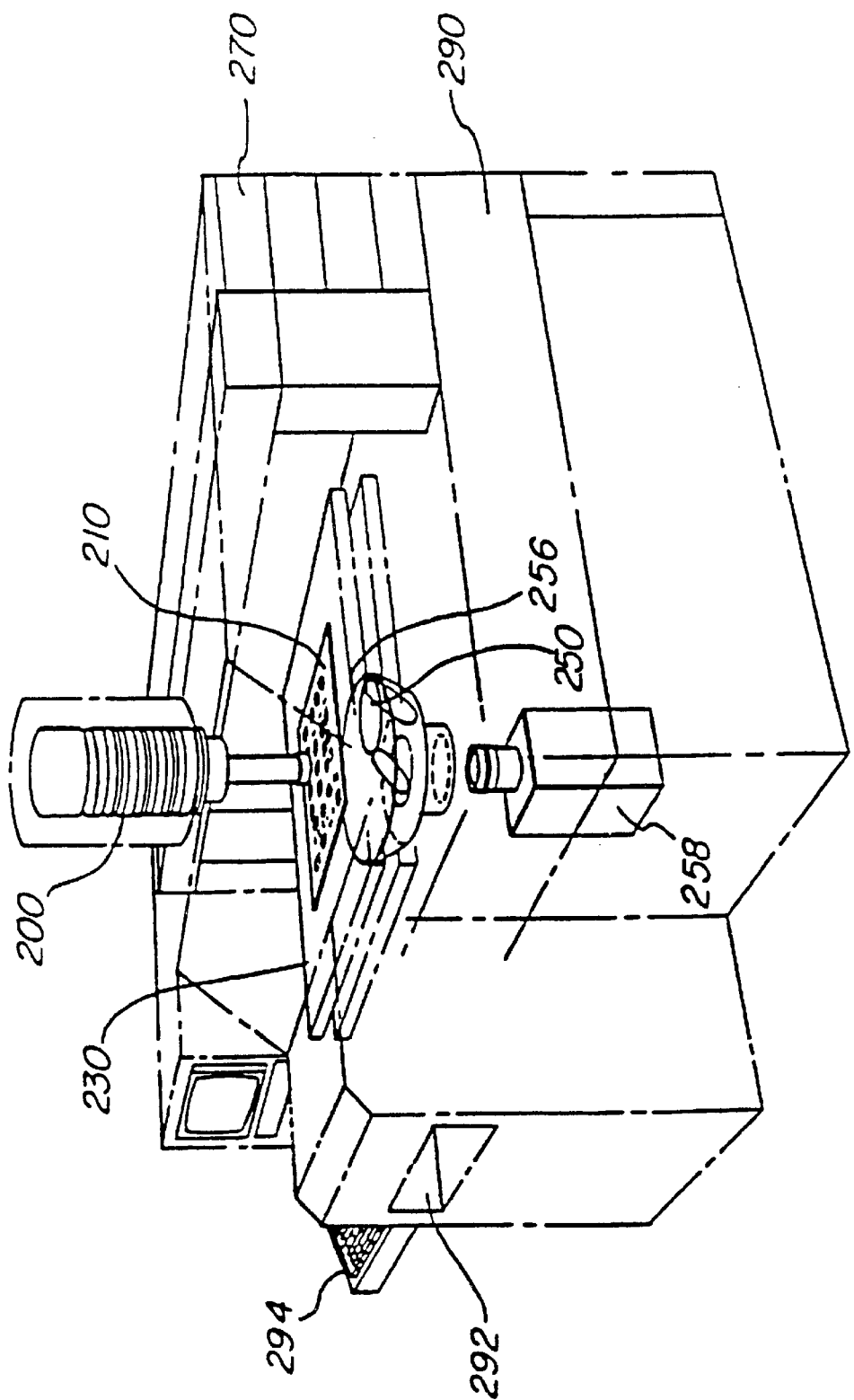

A perspective view of the laminographic apparatus is shown in FIG. 3c. In addition to the X-ray tube 200, circuit board 210, fluorescent screen 250, turntable 256, camera 258, positioning table 230 and computer 270 shown in FIG. 3a, a granite support table 290, a load/unload port 292 and an operator station 294 are shown. The granite table 290 provides a rigid, vibration free platform for structurally integrating the major functional elements of the laminographic apparatus, including but not limited to the X-ray tube 200, positioning table 230 and turntable 256. The load/unload port 292 provides a means for inserting and removing circuit boards 210 from the machine. The operator station 294 provides an input/output capability for controlling the functions of the laminographic apparatus as well as for communication of inspection data to an operator.

In operation of the laminographic apparatus as shown in FIGS. 3a and 3c, high resolution, cross-sectional X-ray images of the solder joints 214 connecting components 212 on circuit board 210 are acquired using the X-ray laminographic method previously described in reference to FIGS. 1 and 2. Specifically, X-ray tube 200, as shown in FIG. 3a, comprises a rotating electron beam spot 285 which produces a rotating source 280 of X-rays 282. The X-ray beam 282 illuminates a region 283 of circuit board 210 including the solder joints 214 located within region 283. X-rays 284 which penetrate the solder joints 214, components 212 and board 210 are intercepted by the rotating fluorescent screen 250.

Dynamic alignment of the position of the X-ray source 280 with the position of rotating X-ray detector 240 is precisely controlled by feedback system 260. The feedback system correlates the position of the rotating turntable 256 with calibrated X and Y deflection values stored in a look-up table (LUT). Drive signals proportional to the calibrated X and Y deflection values are transmitted to the steering coils 281 on the X-ray tube 200. In response to these drive signals, steering coils 281 deflect electron beam 285 to locations on an annular shaped target anode 287 such that the position of the X-ray source spot 280 rotates in synchronization with the rotation of detector 240 in the manner previously discussed in connection with FIG. 1. X-rays 284 which penetrate the board 210 and strike fluorescent screen 250 are converted to visible light 286, thus creating a visible image of a single plane within the region 283 of the circuit board 210. The visible light 286 is reflected by mirrors 252 and 254 into camera 258. Camera 258 typically comprises a low light level closed circuit TV (CCTV) camera which transmits electronic video signals corresponding to the X-ray and visible images to the computer 270 via line 276. The image analysis feature of computer 270 analyzes and interprets the image to determine the quality of the solder joints 214.

Computer 270 also controls the movement of positioning table 230 and thus circuit board 210 so that different regions of circuit board 210 may be automatically positioned within inspection region 283.

The laminographic geometry and apparatus shown and described with reference to FIGS. 1–3 are typical of that which may be used in conjunction with the present invention. However, specific details of these systems are not critical to the practice of the present invention, which addresses an alternate and/or additional technique for adjusting the Z-axis location of the image plane within the circuit board 210. For example, the number of computers and delegation of tasks to specific computers may vary considerably from system to system as may the specific details of the X-ray source, detector, circuit board positioning mechanism, etc.

Electronic Z-Axis Laminography System

Figure 4:
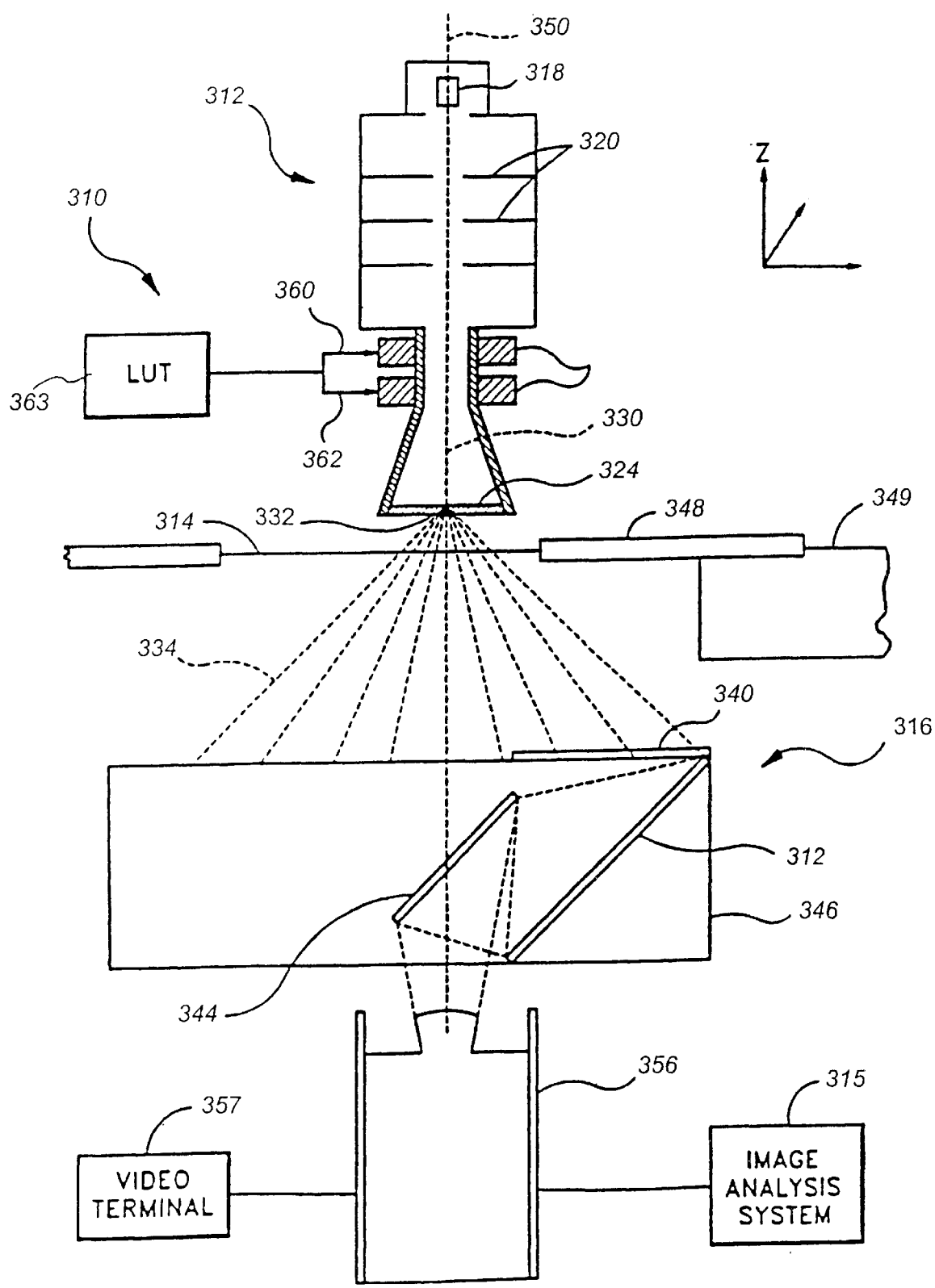
FIGS. 4 and 5 are schematic views of a laminography system in accordance with the present invention.

FIG. 4 illustrates a schematic diagram of a laminography system 310 in accordance with the present invention. The system 310 comprises a source of X-rays 312 positioned above an object 314 to be viewed, and a rotating X-ray detector 316, positioned below the object 314, opposite the X-ray source 312. The object 314 may, for example, be an electronic item such as a circuit board, a manufactured item such as an aircraft part, a portion of a human body, etc.

The invention acquires X,Y plane cross-sectional images of the object 314 under inspection using multipath laminography geometries which enables multiple locations of the object 314 to be sequentially viewed without requiring mechanical movement of the object 314. Movement in various scan circles produces laminographs at the desired X, Y coordinate locations and various Z planes without the need for mechanical movement of the viewed object 314. In one embodiment, the invention may be interfaced with an analysis system 315 which automatically evaluates the cross-section image generated by the system 310 and provides a report to the user that indicates the results of the evaluation.

The source 312 is positioned adjacent the object 314, and comprises an electron gun 318, a set of electrodes for electron beam acceleration and focus 320, a focus coil 360, and a steering yoke or deflection coil 362, and a substantially flat target anode 324. An electron beam 330 emitted from the electron gun 318 is incident upon the target 324, producing an X-ray spot 332 which serves as an approximately point source of X-rays 334. The X-rays 334 originate in the target 324 from the point where the electron beam 330 impinges upon the target 324 and, as described below, illuminate various regions of the object 314.

The object 314 is typically mounted on a platform 348 which may be affixed to a granite table 349, so as to provide a rigid, vibration-free platform for structurally integrating the functional elements of the system 310, including the X-ray source 312 and turntable 346. It is also possible that the platform 348 comprises a positioning table that is capable of moving the object 314 relatively large distances along three mutually perpendicular axes X, Y, and Z.

The rotating X-ray detector 316 comprises a fluorescent screen 340, a first mirror 342, a second mirror 344, and a turntable 346. The turntable 346 is positioned adjacent to the object 314, on the side opposite to the X-ray source 312. A camera 356 is positioned opposite the mirror 344, for viewing images reflected into the mirrors 342, 344 from the fluorescent screen 340. The camera 356 typically comprises a low light level closed circuit television or CCD camera that produces a video image of the X-ray image formed on the fluorescent screen 340. The camera 356 may, for example, be connected to a video terminal 357 so that an operator may observe the image appearing on the detector 340. The camera 356 may also be connected to the image analysis system 315.

The laminography system 310 is advantageously encased by a supporting chassis (not shown) which acts to prevent undesired emissions of X-rays, as well as facilitating the structural integration of the major elements of the system 310.

In operation, X-rays 334 produced by the X-ray source 312 illuminate and penetrate regions of the object 314 and are intercepted by the screen 340. Synchronous rotation of the X-ray source 312 and detector 316 about an axis 350 causes an X-ray image of a plane 352 (see FIG. 5) within the object 314 to be formed on the detector 316. Although the axis of rotation 350 illustrated is the common axis of rotation for both the source 312 and detector 316, one skilled in the art will recognize that it is not necessary for the axes of rotation to be collinear. In practice, it is sufficient that the axes of rotation be parallel. X-rays 334 which penetrate the object 314 and strike the screen 340 are converted into visible light reflected by the mirrors 342, 344 and into the camera 356.

Figure 5:
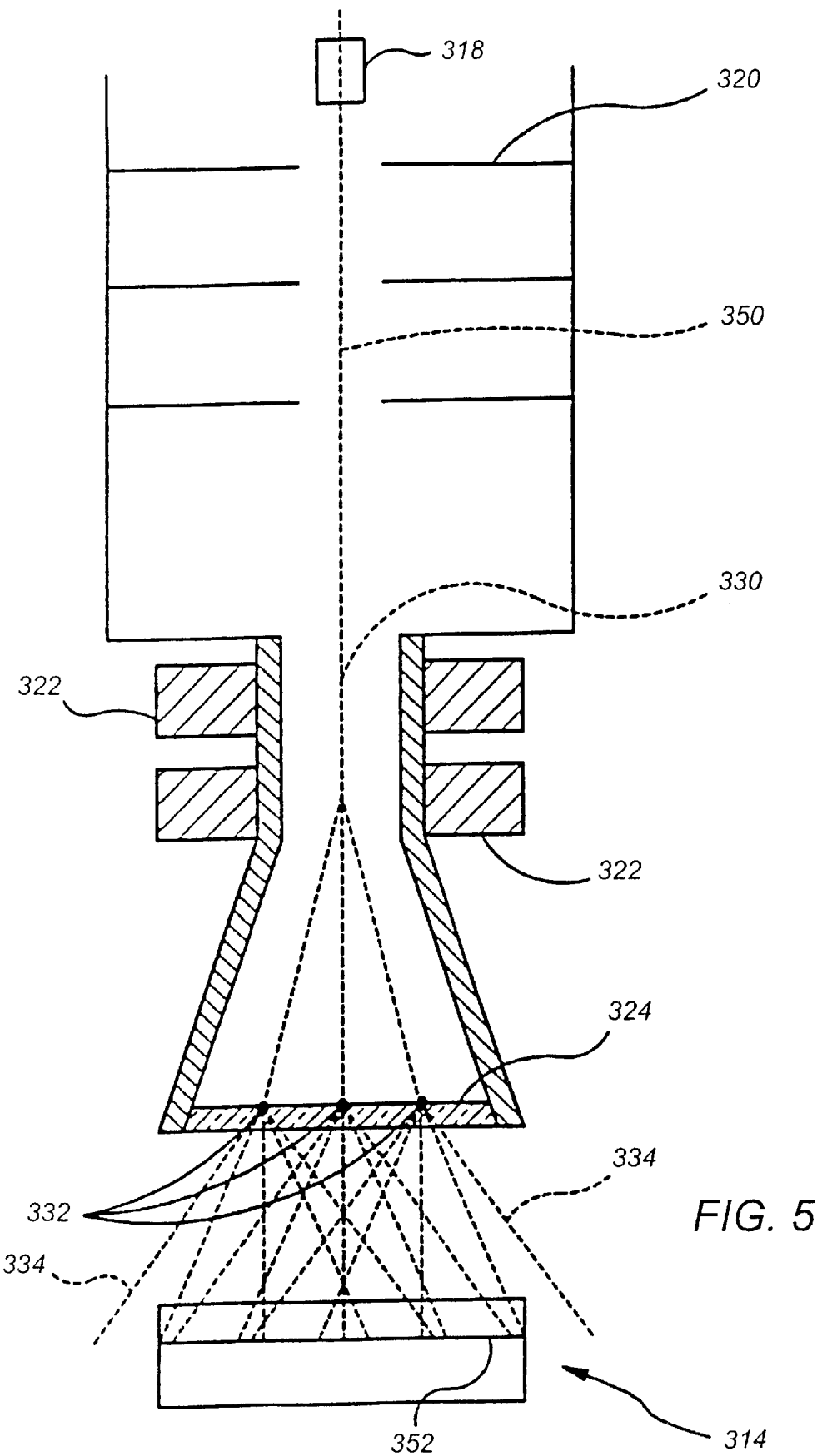

Referring to FIG. 5, the electron beam 330 is emitted from the electron gun 318 and travels in a region between the electrodes 320 and steering coils 322. The electrodes 320 and coils 322 produce electromagnetic fields which interact with the electron beam 330 to focus and direct the beam 330 onto the target 324 forming an electron beam spot 332 from which X-rays are emitted. Preferably, the size of the electron beam spot 332 on the target is on the order of 0.02 to 10 microns in diameter. The steering coils 322 enable the X-ray source 312 to provide X-rays 334 from the X-ray spots 332 wherein the location of the spots 332 move in a desired pattern around the target 324. Preferably, the steering coils 322 comprise separate X and Y electromagnetic deflection coils 360, 362 which deflect the electron beam 330 discharged from the electron gun 318 in the X and Y directions, respectively. Electrical current flowing in the steering yoke 362 creates a magnetic field which interacts with the electron beam 330 causing the beam 330 to be deflected. However, one skilled in the art will also recognize that electrostatic deflection techniques could also be used to deflect the electron beam 330.

Preferably, a LUT 363 outputs voltage signals which, when applied to the X and Y deflection coils 360, 362 cause the electron beam spot 332 to rotate, thus producing a circular pattern on the surface of the target 324. In one embodiment, the LUT 363 provides the output voltages in response to addressing signals from a master computer (not shown) which may be included within the image analysis system 315. The output voltages are advantageously predetermined using a calibration technique which correlates the position of the turntable 346, and the position of the X-ray beam spot 332.

The present invention provides a method and apparatus for processing laminographic images of various Z-axis levels of the object 314 which requires little or no physical movement of the object 314 or the supporting table 348. In accordance with the present invention, desired Z-axis levels of the object are brought within the field of view of the system electronically as opposed to mechanically. This is accomplished by moving the location of the pattern traced by the X-ray beam spot 332 on the target 324. In this manner, various Z-axis levels of the object 314 are brought within the field of view and images are produced of a specific Z-axis level of the object coinciding with the field of view. In accordance with the present invention, the voltages applied to the X and Y deflection coils 360, 362 are varied in order to produce rotating X-ray beam paths of distinct radii having distinct x, y locations on the target 324.

Figure 6:
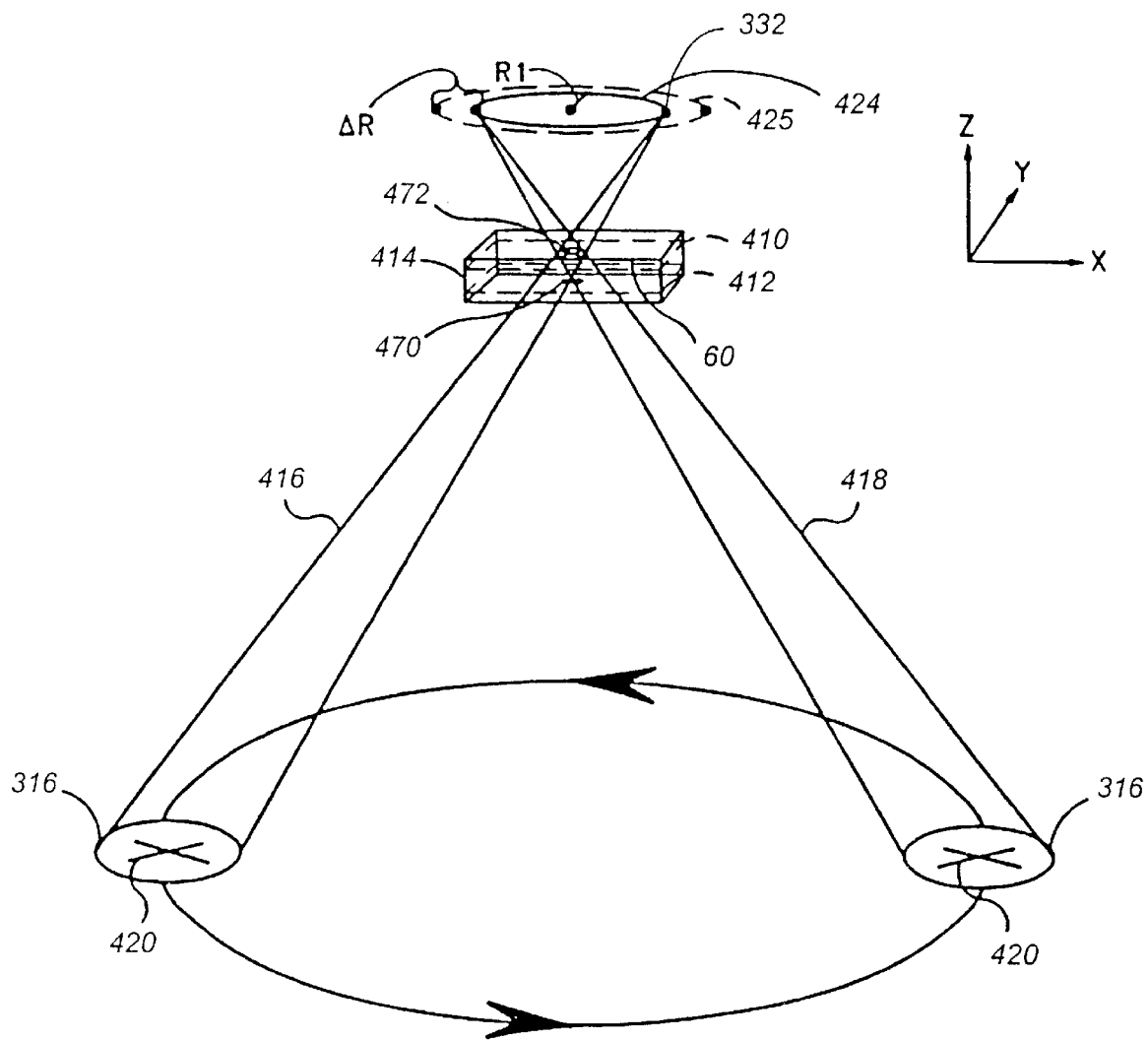
FIGS. 6 and 7 illustrate the manner in which a laminographic system in accordance with the present invention is utilized to produce a Z-axis shaft of the imaged region of the object plane with respect to the object.
Figure 7:
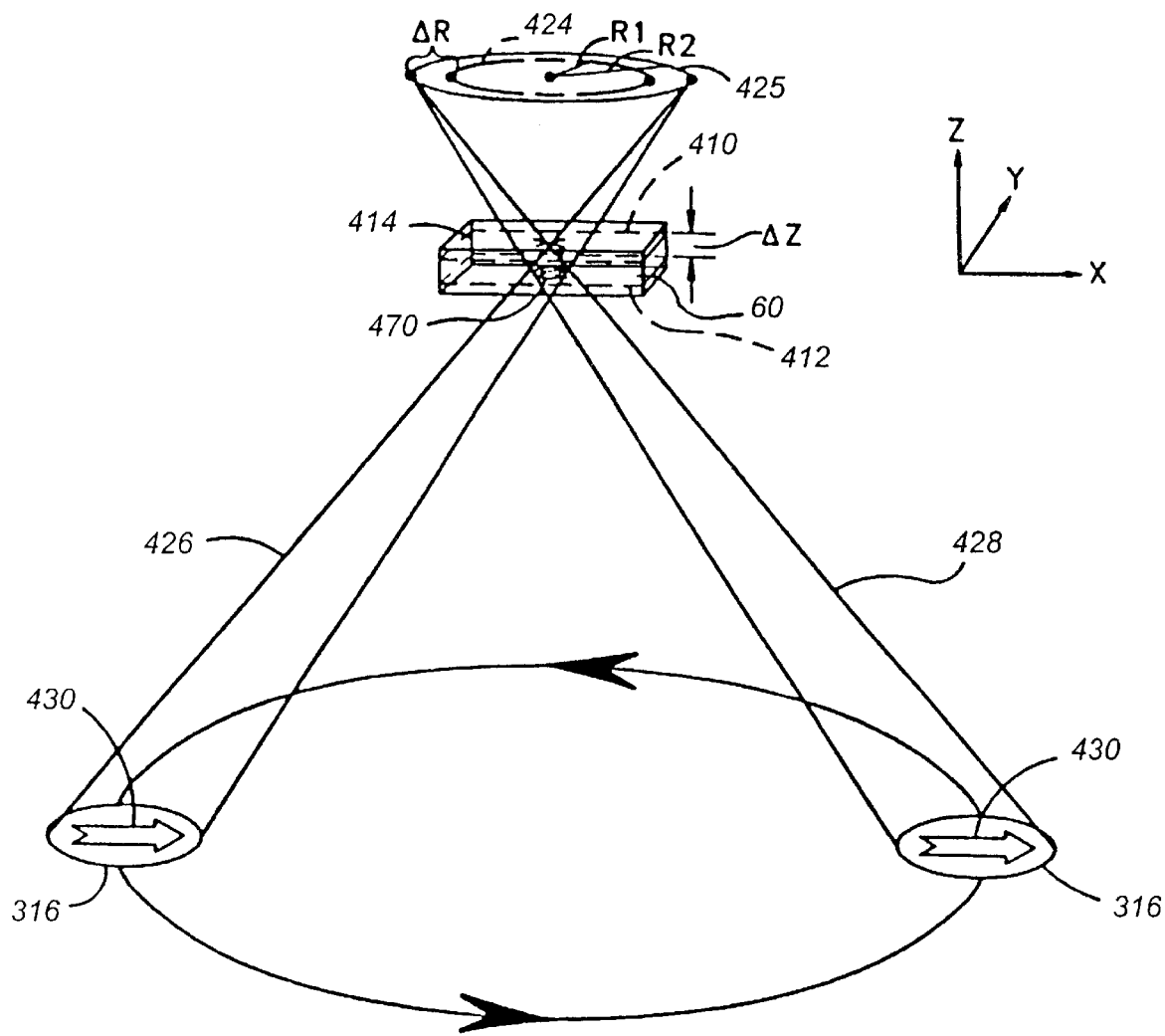

Referring to FIG. 6 and FIG. 7, the present invention further provides a laminography system having a geometry which can be utilized to effect a shift or change in the Z-axis position of the object plane 60 (see FIG. 1) within a test object 414 without moving the test object. FIG. 6 illustrates an object 414 having the patterns of an arrow 470 and a cross 472 located therein. The cross pattern 472 is located in a first plane 410 and the arrow pattern 470 is located in a second plane 412, wherein the first plane 410 lies above and is parallel to the second plane 412. The X-ray beam spot 332 traces a scan circle 424 having a radius R1, defining a family of cones including cones 416, 418.

The intersection of the cones formed as the X-ray beam spot 332 travels around the circle 424, including cones 416, 418, forms an image region substantially centered about the cross pattern 472, such that the first plane 410 is defined as the object plane 60. As the X-ray spot 332 and detector 316 rotate in synchronization, a distinct image 420 of the cross pattern 472 is produced on the surface of the detector 316. The image of the arrow 470, which lies in the second plane 412 and is outside the object plane 410 defined by the cones 416, 418, is not stationary on the detector 316 during the entire rotation of the detector 316 and thus, appears blurred.

FIG. 7 illustrates that by adjusting the gain of the voltages output from the LUT 363 to the deflection coils 360, 362, thereby changing the amplitude of sine and cosine signals driving the coils, the radii of the scan circles 424, 425 traced by the X-ray spot 332 can be varied to produce images of regions within distinct Z-axis planes in the object 414. With the adjustment of the gain applied to the output from the LUT 363, the scan circle 424 is increased in radius by a value ΔR to a radius R2, thereby forming a scan circle 425 defining a second family of cones including the cones 426, 428. Because of the larger radius R2 of the second scan circle 425, the set of points defined by the intersection of a second family of cones, including cones 426, 428, is displaced in the negative Z direction relative to the region imaged when the X-ray source 332 follows the path 424 (FIG. 6). Thus, the object plane 60 is lowered by an amount ΔZ to the second plane 412, and the image region is substantially centered about the arrow pattern 470. As the X-ray spot 332 and detector 316 rotate, a distinct image 430 of the arrow pattern 470 is then produced on the detector 316, while the image of the cross pattern 472, lying outside the object plane 412, appears blurred. The amplitude of the gain adjustment made to the voltages applied to the deflection coils 360, 362 is proportional to the direction and amount of the shift ΔZ in the position of the object plane 60, 410, 412. For example, a large increase in the gain would result in a relatively large movement of the object plane 60 in the downward (i.e., negative Z) direction, while a small decrease in the gain would result in a relatively small movement of the object plane 60 in the upward (i.e., positive Z) direction. In this manner, the geometry utilized in the laminographic system of the present invention further allows various planes in the object 414 to be imaged upon the detector 316 without mechanical movement of any of the system components.

Figure 8:
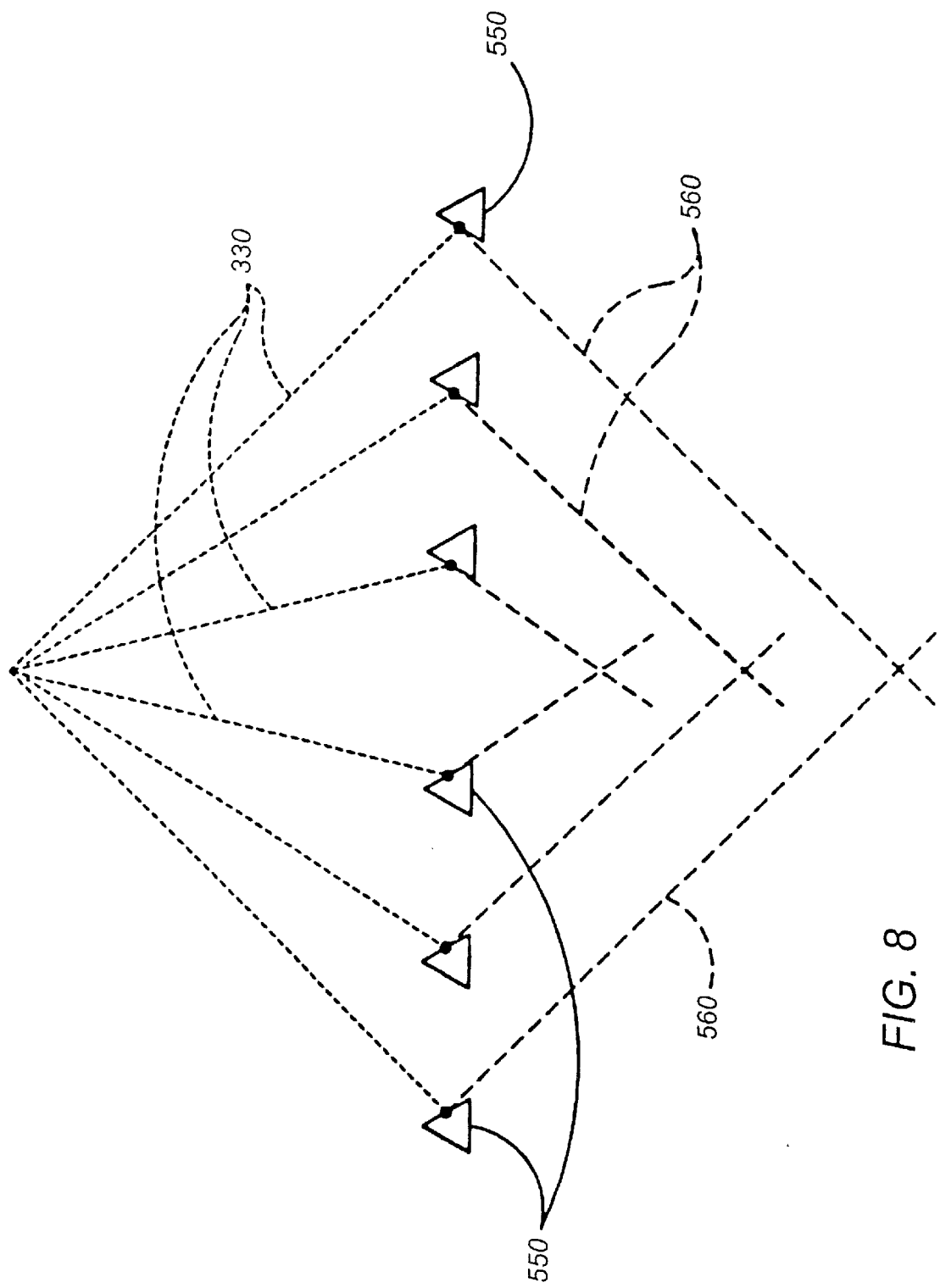
FIG. 8 illustrates a possible configuration of a X-ray target anode which may be used with the present invention.

It will be understood that different configurations of the target anode 324 may be used in accordance with the present invention. For example, FIG. 8 illustrates an embodiment of a target anode that may be used in accordance with the present invention. FIG. 8 shows a cross-sectional view of this embodiment of the target. In the embodiment shown in FIG. 8, a target 550 comprises multiple concentric rings which are formed so that X-rays 560 are produced when the electron beam 330 is incident upon the surface of the target 550. Each of the rings has a different radius so that objects in different focal planes along the Z-axis are imaged when the electron beam 330 is deflected to trace a path on selected ones of the rings of the target 550.

Laminographic and Magnification Geometries

FIG. 1 shows the parameters referred to in the following discussion and equations regarding the laminographic geometry of the present method and device. The radius of the circular path followed by the rotating X-ray detector 30 is "$R_0$" and maintains a constant value. Similarly, the Z-axis distance between the rotating X-ray source 20 (X-ray tube target) and the rotating X-ray detector 30 is "$Z_0$" and maintains a constant value. The radius of the circular path followed by the rotating source of X-rays 20 is "r" and is a variable in the geometry used for the present invention. The central X-ray path 50 from the X-ray source 20 forms an angle "θ" with the common axis of rotation 40. The Z-axis distance between the image plane 60 in object 10 and the X-ray detector 30 is "z". The distance "z" is determined by the intersection 70 of the central X-ray path 50 with the common axis of rotation 40. Thus, a change in the radius "r" of the circular path followed by the rotating source of X-rays 20 also results in changes in the angle "θ", the Z-axis location of the image plane 60, i.e., the point of intersection 70, and the Z-axis distance "z" between the image plane 60 and the X-ray detector 30. The equations to determine the radius "r" required for a specified distance "z" are straightforward as follows:

$$z = R_0/\tan\theta = (R_0/r)(Z_0 - z) \quad (1)$$

Solving equation (1) for the radius "r" in terms of the Z-axis distance "z" results in the following:

$$r = -(R_0/z)(Z_0 - z) = R_0\left(\frac{Z_0}{Z} - 1\right) \quad (2)$$

In one configuration of the present invention, the radius "r" of the circular path followed by the rotating source of X-rays 20 is adjusted in accordance with equation (2) to electronically change the position of the Z-axis location "z" of the image plane 60 with respect to the X-ray detector 30. This results in a laminography system which does not require a mechanical system to change the Z-axis location "z" of the image plane 60 with respect to the X-ray detector 30. For example, in the laminographic inspection of a circuit board, cross-sectional images of different Z-axis positions of the circuit board (including both top and bottom surfaces and any other slices), may be brought into the image plane 60, by electronically shifting the radius of rotation "r" of the rotating source of X-rays 20 as opposed to mechanically moving the circuit board in the Z-axis direction.

Changing the Z-axis position "z" of the circuit board image plane 60 by changing the radius of rotation "r" of the rotating source of X-rays 20, also results in changing the Field of View (FOV) of the image formed on detector for different values of "r" and "z". As previously discussed, the phrase "Field of View" or "FOV" as used herein refers to the size of a particular region or area of a circuit board which is included in a laminographic image of th at particular region or area of the circuit board. Thus, the size of the image changes with respect to the region or area of the circuit board being inspected, i.e., the magnification of the image changes when "r" and "z" change. This change in FOV and hence magnification factor must be accurately and efficiently accounted for in a circuit board inspection laminography system.

There are several ways that these changes in FOV with magnification can be accounted for and corrected in analyzing the images. In circuit board inspection systems, CAD data which describes the circuit board being inspected is utilized during the acquisition and analysis of the images of the circuit board. Thus, a first technique for compensating for variable image magnification factors and FOV's may be accomplished by magnifying or shrinking the acquired images to a "nominal" size ("nominal" being defined by a base FOV). Numerous algorithms for doing this are well documented in the technical literature. However, these techniques tend to be CPU intensive and may affect throughput of the system. A second and preferred technique for compensating for variable image magnification factors and FOV's may be accomplished more efficiently by using on-the-fly CAD data manipulation and on-the-fly FOV adjustments during the analysis of the images.

Figure 9:
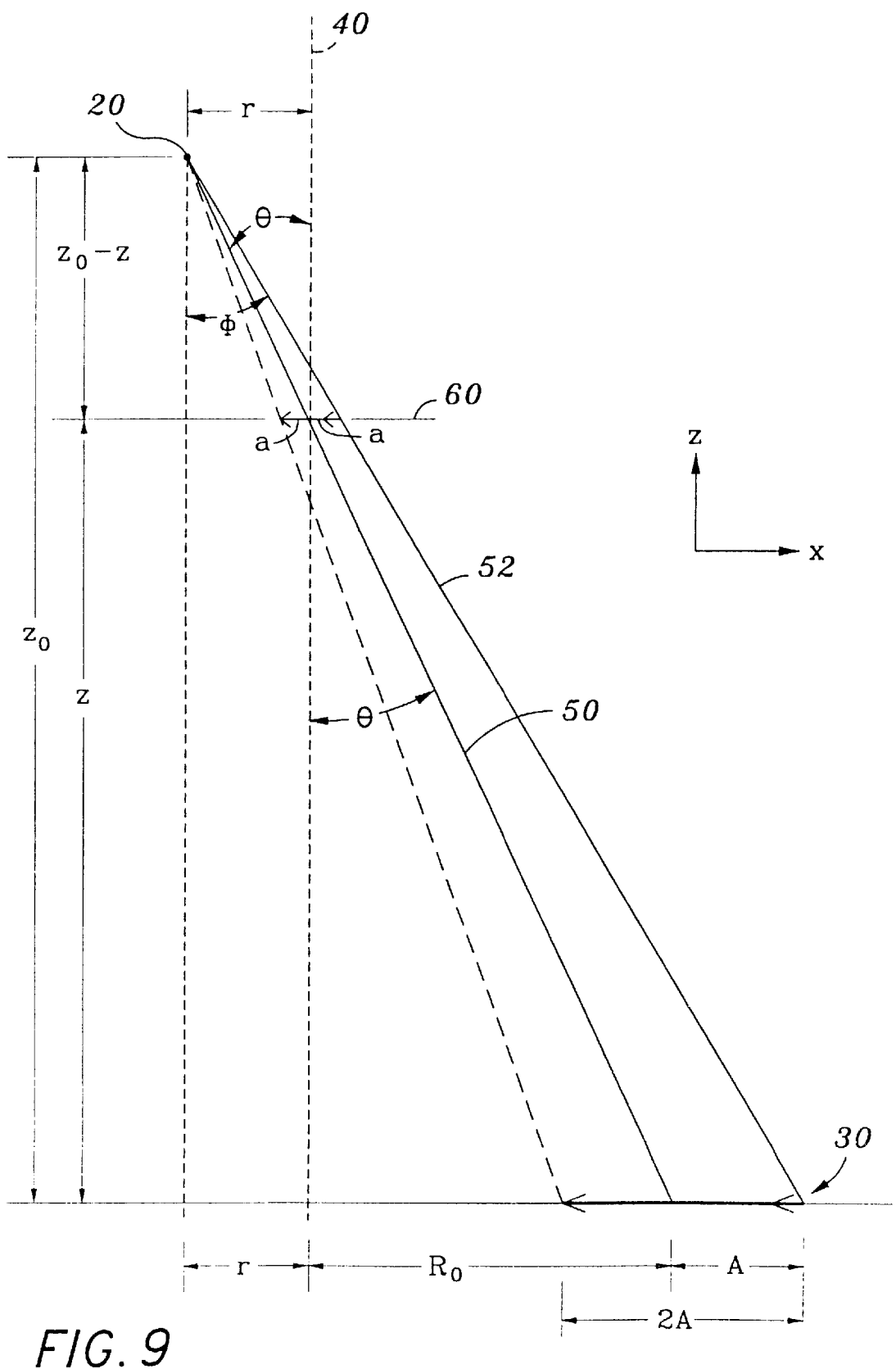
FIG. 9 illustrates how the magnification of an image is related to the distance between an image plane and an X-ray detector.

FIG. 9 illustrates how the magnification of an image is related to the distance "z" between the image plane 60 and the X-ray detector 30. Image magnification is defined as the ratio of the size of the image to the size of the object which forms the image. For example, FIG. 9 shows an object being imaged in the form of an arrow having a linear dimension "2a" in the image plane 60. The image of the arrow is shown in the plane of the X-ray detector 30 and has a linear dimension "2A". Thus, the magnification is given by "A/a". The arrow object is positioned in the XZ plane such that the common axis of rotation 40 bisects the arrow in the X-axis direction. Thus, half the length of the arrow, "a", lies on a first side of the axis 40 and the other half lies on a second side of the axis 40. The following equations show how the magnification of the image is related to geometric parameters of the inspection system. As previously shown in FIG. 1, the radius of the path followed by the X-ray source 20 about the common axis of rotation 40 is "r", the angle formed between a central ray 50 from X-ray source 20 and the common axis of rotation is "θ", the Z-axis distance between the X-ray source 20 and the plane of the X-ray detector 30 is "$Z_0$", the Z-axis distance between the image plane 60 and the plane of the X-ray detector 30 is "z", and the Z-axis distance between the X-ray source 20 and the image plane 60 is "($Z_0$ z)". A reference angle "φ" with respect to the vertical axis of rotation 40 is formed between an X-ray projection 52 from the X-ray source 20 to a first end of the arrow object. The derivation of the magnification of the image, "A/a", in terms of "A", "a", "$Z_0$" and "z" is as follows:

$$\tan\phi = \frac{a+r}{Z_0 - z} = \frac{A + R_0 + r}{Z_0} \quad (3)$$

$$(a+r)Z_0 = (A + R_0 + r)(Z_0 - Z) \quad (4)$$

$$aZ_0 + rZ_0 = A(Z_0 - z) + R_0(Z_0 - z) + r(Z_0 - z) \quad (5)$$

$$aZ_0 = A(Z_0 - z) + R_0(Z_0 - z) - rz \quad (6)$$

Using equation (2) for "r" in terms of "z", equation (6) becomes:

$$aZ_0 = A(Z_0 - z) + R_0(Z_0 - z) - R_0(Z_0/z - 1)z\, 1 \quad (7)$$

Which results in a magnification factor A/a of:

$$\frac{A}{a} \cdot \frac{Z_0}{Z_0 - z} \quad (8)$$

It is to be understood that the above discussion, although presented in terms of one dimension for purposes of illustration, applies equally to the second dimension of the image plane 60 and the plane 64 of the X-ray detector 30. Since square or rectangular electronic detectors are more readily available than circular detectors, corresponding square or rectangular images are selected for analysis. Additionally, square or rectangular patterns are more readily adapted to computer analysis than are other shapes, e.g., circular patterns. However, the present invention is also applicable to systems which use detectors and images which are not square or rectangular, including circular detectors and images.

The following specific example of a system having two pre-defined magnifications further illustrates the geometry discussed above. In this example, a square portion of the image formed on the X-ray detector 30 is selected. The selected square image has a length and a width of "2A", which in this example is selected to be approximately equal to 3.8 inches. The FOV corresponding to the 2A by 2A (3.8 inches×3.8 inches) image, i.e., the particular region in the image plane 60 of the object being inspected, e.g., a circuit board, has a length and width of "2a", the size of which varies with the size of the radius "r". Other fixed dimensions for this example include the radius of the circular path followed by the rotating X-ray detector 30, "$R_0$", which is selected to be approximately equal to 5.8 inches, and the Z-axis distance between the rotating X-ray source 20 (X-ray tube target) and the rotating X-ray detector 30, "$Z_0$", which is selected to be approximately equal to 12.5 inches. A first magnification factor, MAG 1, of approximately 19× is achieved at a radius "r" of approximately 0.32 inches. The first magnification factor, MAG 1, has an FOV of approximately of 0.2 inches×0.2 inches in image plane 60 and a Z-axis distance between the image plane 60 and the plane 64 of the X-ray detector 30 "z" of approximately 11.84 inches. Similarly, a second magnification factor, MAG 2, of approximately 4.75× is achieved at a radius "r" of approximately 1.55 inches. The second magnification factor, MAG 2, has an FOV of approximately of 0.8 inches×0.8 inches in image plane 60 and a Z-axis distance between the image plane 60 and the plane 64 of the X-ray detector 30, "z", of approximately 8.87 inches. The MAG 1 and MAG 2 configurations are summarized in Table 1 below.

TABLE 1

| | MAG 1 | MAG 2 |
|---|---|---|
| Field of View - FOV (2a × 2a) | 0.2" × 0.2" | 0.8" × 0.8" |
| Z-axis Distance between Image plane 60 X-ray Detector Plane 30 (z) | 0.32" | 1.55" |
| Magnification Factor (A/a) | 19x | 4.75x |
| Detected Image Size (2A x. 2A) | 3.8" x. 3.8" | 3.8" × 3.8" |
| Rotating X-ray Detector Radius ($R_0$) | 5.8" | 5.8" |
| Distance between X-ray Source and X-ray Detector ($Z_0$) | 12.5" | 12.5" |

Circuit Board Inspection Using Electronic Z-Axix Laminography Systems

There are two primary options for using the above described electronic Z-axis laminography system for inspection of electrical connections (e.g., solder joints) on circuit boards. The first option supports the circuit board at a single fixed Z-axis position in the system and varies the radius of the X-ray source to obtain laminographic images at all other Z-axis locations of interest. The second option provides mechanical supports for the circuit board at multiple fixed Z-axis positions in the system and varies the radius of the X-ray source to obtain laminographic images at Z-axis locations intermediate the fixed locations.

The first option includes a laminography system having a mechanical support for the circuit board which is located at a single, i.e., fixed, Z-axis position in the system. While the circuit board support does not allow for movement of the circuit board along the Z-axis of the system, it does provide for precise positioning of the circuit board along the X and Y axes of the system, wherein the XY plane is substantially parallel to the plane of the circuit board. In this system, one base or "central" FOV in a single fixed image plane 60 corresponding to the fixed Z-axis location is selected. Laminographic images of portions of the electrical connections on the circuit board which are either above or below the fixed Z-axis image plane are acquired by changing the radius of the rotating X-ray source as described above. Thus, perturbations to the fixed base or central FOV at the fixed Z-axis location allows for acquisition of laminographic cross-sectional images of regions above and below the fixed Z-axis position.

Figure 10:
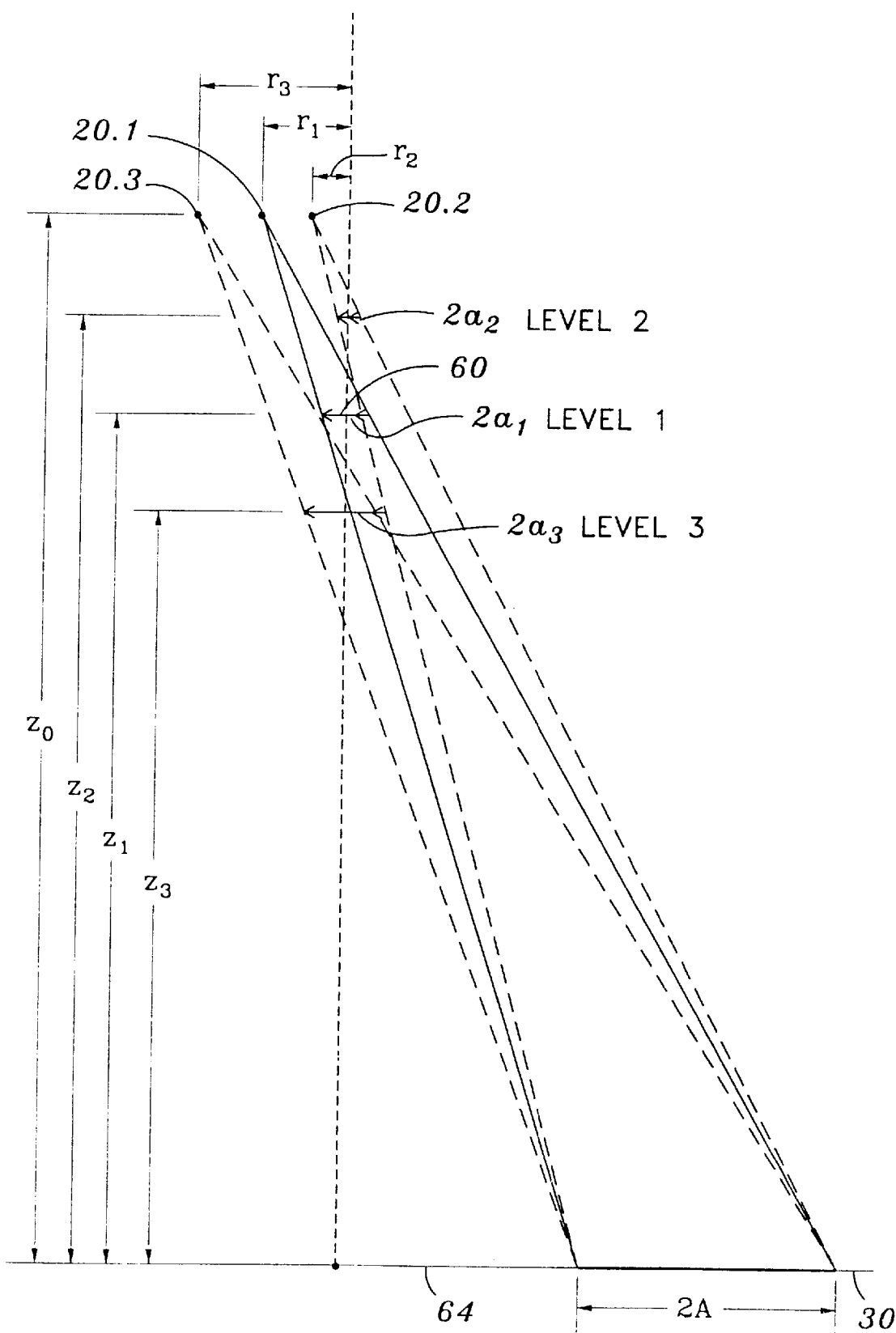
FIG. 10 illustrates how the FOV and magnification changes in a first implementation of the present invention.

An example of the first option is illustrated in FIG. 10. The circuit board is positioned in the laminography system such that an approximate midpoint thickness level of the region of the circuit board (or electrical connection on the circuit board) being inspected approximately coincides with the fixed image plane referred to as Level 1 in FIG. 10. The Z-axis distance between the rotating X-ray source positions 20.1, 20.2, 20.3 and the plane 64 of the X-ray detector 30 is "$Z_0$", the Z-axis distance between the image plane 60 and the plane 64 of the X-ray detector 30 is "z", and the Z-axis distance between the X-ray source positions 20.1, 20.2, 20.3 and the image plane 60 is "$(Z_0-z)$". The base or "central" FOV in fixed image plane 60, i.e., Level 1, is located at a distance $z_1$, from the plane 64 of the X-ray detector 30 and is characterized by: a first magnification factor; a first radius "$r_1$," of the rotating X-ray source 20.1; a first FOV having dimensions of $2a_1 \times 2a_1$, in image plane 60; and a Z-axis distance between the image plane 60 and the plane of the rotating X-ray source 20.1 of "$(Z_0-z_1)$". A second FOV, i.e., Level 2, is located above Level 1 at a distance $z_2$ from the plane 64 of the X-ray detector 30 and is characterized by: a second magnification factor; a second radius "$r_2$" of the rotating X-ray source 20.2; a second FOV having dimensions of $2a_2 \times 2a_2$ in image plane 60; and a Z-axis distance between the image plane 60 and the plane of the rotating X-ray source 20.2 of "$(Z_0-z_2)$". A third FOV, i.e., Level 3, is located below Level 1 at a distance $z_3$ from the plane 64 of the X-ray detector and is characterized by: a third magnification factor; a third radius "$r_3$" of the rotating X-ray source 20.3; a third FOV having dimensions of $2a_3 \times 2a_3$ in image plane 60; and a Z-axis distance between the image plane 60 and the plane of the rotating X-ray source 20.3 of "$(Z_0-z_3)$". Similarly, laminographic images at levels intermediate Levels 1 and 2 and Levels 1 and 3 may be acquired by selecting the appropriate radius of the rotating X-ray source 20 in accordance with equation (2).

Applying the above example to a typical circuit board further illustrates this system. In this specific example, the base or "central" FOV, is selected to correspond to the specific system configuration referred to as MAG 2 as summarized in Table 1. The Z-axis levels of interest for a typical electrical connection inspection are generally located within a range of approximately ±60 mils (0.060 inch) centered about a central Z-axis level. Equation (2) is used to derive the value of the X-ray source radius for each specific Z-axis level. Equation (8) is used to derive the value of the Magnification factor for each specific Z-axis level. Examples of specific parameters for Levels 1, 2 and 3 of this configuration are presented in Table 2. Laminographic images at levels intermediate Levels 1 and 2 and Levels 1 and 3 may be acquired by selecting the appropriate radius of the rotating X-ray source 20 between 1.50 inches and 1.59 inches in accordance with equation (2). Similarly, lamino-graphic images at levels above Level 2 and/or below Level 3 may be acquired by selecting the appropriate radius of the rotating X-ray source 20 in accordance with equation (2).

TABLE 2

|  | Level 2 | Level 1 | Level 3 |
| --- | --- | --- | --- |
| FOV (2a × 2a) | 0.78" × 0.78" | 0.80" × 0.80" | 0.82" × 0.82" |
| X-ray Radius (4) | 1.50" | 1.55" | 1.59" |
| Image Plane-to-Detector (z) | 9.93" | 9.87" | 9.81" |
| Magnification Factor (A/a) | 4.86x | 4.75x | 4.65x |
| Image Size (2A × 2A) | 3.8" x. 3.8" | 3.8" x. 3.8" | 3.8" x. 3.8" |
| X-ray Detector Radius ($R_0$) | 5.8" | 5.8" | 5.8" |
| X-ray Source-to-Detector ($Z_0$) | 12.5" | 12.5" | 12.5" |

The second option includes a laminography system which provides mechanical supports for the circuit board at multiple fixed Z-axis positions in the system and varies the radius of the X-ray source to obtain laminographic images at Z-axis locations intermediate the fixed locations. An example of the second option involves a simplified Z-axis that allows 2 or more discreet "stops" so that multiple FOVs can be used for magnification purposes. For example, fine pitch devices often require higher magnification than larger discreet components like passive devices (e.g., chip capacitors and resistors). Using the specific example illustrated in Table 1, this type of system could have a first fixed position which magnifies the image by a factor of 4.75 for inspections of the large components on the circuit board and a second fixed position which magnifies the image by a factor of 19 for inspections of the smaller fine pitch devices on the circuit board. Thus, this simplified dual-position design still provides for inspections at any value of Z within the designed inspection range of the system, but no longer requires on-the-fly accurate high-speed Z positioning at any continuous value of Z within the designed inspection range of the system.

On-The-Fly CAD Data Manipulation

Circuit board inspection systems typically include data files that describe the positions, size, pin locations, and other important design data for all inspected solder joints and other features in all board views. As previously stated, the phrase "board view" refers to the laminographic image of a particular region or area of the circuit board identified by a specific X,Y coordinate of the circuit board. A complete inspection of a circuit board typically includes multiple board views. Additionally, some board views include multiple slices, i.e., cross-sectional images acquired at different Z height locations or layers of the circuit board.

In prior art inspection systems, the image plane of the inspection system may include several fixed Z-axis locations, one for each calibrated FOV, and the multiple image slices of the circuit board within one of the FOV's at different Z-levels with respect to the circuit board are acquired by mechanically moving the circuit board along the inspection system Z-axis such that the desired Z-level slice of the circuit board coincides with the fixed inspection system Z-axis location of the image plane for that FOV. Since the inspection system Z-axis location of the image plane is fixed, and the multiple image slices of the circuit board at different Z-levels with respect to the circuit board are positioned at this fixed inspection system Z-axis location, all of the images acquired at this fixed inspection system Z-axis location have the same FOV and magnification. However, as previously described, the present invention replaces the mechanical movement of the circuit board along the Z-axis of the inspection system with electrically controlled relocation of the image plane along the Z-axis of the inspection system. As previously described, this results in image planes positioned at different Z-axis locations of the inspection system having different FOV's and magnifications. The present invention compensates for these changes in FOV and magnification by modifying the CAD design data on-the-fly to match the magnification of the current image.

In the present context, "on-the-fly" data analysis refers to real time or near real time modification of the CAD data on as-needed basis for analysis of the current image as opposed to modifying the CAD data in advance and storing it for later recall and utilization. Analysis of the image is then carried out in the normal manner, i.e., comparing the acquired image data with the CAD design data, using the modified CAD data. For example, one situation where on-the-fly CAD data modification is advantageous is where surface mapping of the boards before inspection reveals that each new circuit board is likely to have different Z heights with respect to the inspection system for the same specific Z level within a specific solder joint. These variations in Z heights with respect to the inspection system from board to board are most commonly due to variations in board warpage measured by laser range finder readings from board to board. In other words, board warpage causes a Z level referenced to the circuit board surface to be located at different Z-axis levels of the laminographic inspection system. Thus, electronic relocation of the image plane with respect to the inspection system coupled with on-the-fly CAD data modification provides a processor time and data storage resource efficient means for acquiring images at the desired Z levels of the circuit board and analyzing these images by recalling, modifying and applying the CAD data for use on an as needed basis.

On-the-fly CAD data manipulation requires that various CAD data fields be modified. The CAD data fields requiring modification depends on the current FOV. Examples of specific CAD files which often require modification are discussed below. The CAD data files discussed below are included to illustrate the procedure and are not to be considered as limiting which files may be subject to modification when practicing the present invention. The present invention is applicable to virtually any type of CAD data which may be required for laminographic electrical connection or solder joint inspection.

Conversions: Pixels to Mils and Mils to Pixels

Conversion of image units, e.g., pixels, to physical dimensionals, e.g., mils, is accomplished by dividing the physical size of the current FOV by the number of pixels included in an image frame buffer width as follows:

PixelsToMils=
    Current $FOV$ in mils/Frame Buffer Width in pixels    (9)

This is illustrated by a specific example where the number of pixels in an image is 2048×2048 and the image corresponds to a region of an object having physical dimensions of 800 mils×800 mils (0.8 inches×0.8 inches). The PixelsToMils conversion factor for this example is determined from equation (9) by dividing 800 mils by 2048 pixels, yielding a PixelsToMils conversion factor which is approximately equal to 0.391 mils. Thus, the width of each pixel in the image corresponds to a width of approximately 0.391 mils on the object shown in the image.

Similarly, the inverse conversion from physical dimensionals, e.g., mils, to image units, e.g., pixels, is accomplished by dividing the number of pixels included in an image frame buffer width by the physical size of the current FOV as follows:

MilsTopixels=
    Frame Buffer Width in pixels/Current $FOV$ in mils    (10)

Using the previous specific example where the number of pixels in the image is 2048×2048 and the image corresponds to a region of an object having physical dimensions of 800 mils×800 mils, the MilsToPixels conversion factor is determined from equation (10) by dividing 2048 pixels by 800 mils, yielding a MilsToPixels conversion factor which is approximately equal to 2.56 pixels. Thus, a width of approximately 1 mil on the object corresponds to approximately 2.56 pixels in the image of the object.

Conversion of CAD Coordinates to Pixels

It is generally advantageous to perform on-the-fly calculations for coordinating and comparing CAD data with image data in pixel coordinate format. However, the primary format for CAD data received by the inspection facility is generally in physical dimensions format (e.g., mils). Thus, the physical dimensions format CAD data is converted to pixel format using equation for the conversion of Mils-To-Pixels. Since coordination and comparison of the CAD data with the image data is generally performed in pixel coordinate format, the following discussion is presented in terms of pixel coordinate format. However, if physical dimensions format is preferred for a particular application, the present invention may also be practiced in physical dimension format.

FOV Correction Factor

A "nominal FOV" or reference FOV refers to a field of view which is used as a reference for calibration of other FOV's of the laminography inspection system. For example, a laminography inspection system may be configured such that the nominal/reference FOV corresponds to an image having a specific magnification factor of an area in the image plane having a specific size. In certain situations, it may be advantageous for a laminography inspection system to have multiple configurations and corresponding multiple nominal FOVs or reference FOVs. For example, referring to the example of a specific laminography system summarized in Table 1, this system has a first nominal/reference FOV (MAG 1) which creates a 3.8 inch×3.8 inch image on 5 a detector which corresponds to an area in the image plane which is 0.2 inch×0.2 inch in size. Thus, this first nominal/reference FOV has a magnification factor of 19. Similarly, this system also has a second nominal/reference FOV (MAG 2) which creates a 3.8 inch×3.8 inch image on a detector which corresponds to an area in the image plane which is 0.8 inch×0.8 inch in size. Thus, this second nominal/reference FOV has a magnification factor of 4.75.

The fields of view and magnification factors for Z-axis locations which are different from the Z-axis location for a nominal/reference FOV are referred to in this discussion as a "current FOV". Thus, if an image is acquired at a "current FOV" which does not coincide with a "nominal FOV", the CAD data must be adjusted to reflect the differences (e.g., magnification, etc.) between the nominal FOV and the current FOV before the image data in the current FOV can be compared to the CAD design data. This FOV conversion of the CAD data from a nominal FOV to a current FOV is done on-the-fly and uses a conversion factor referred to as "FOV Correction" which is calculated as follows:

$FOV$Correction=Nominal$FOV$/Current$FOV$    (11)

Figure 11:
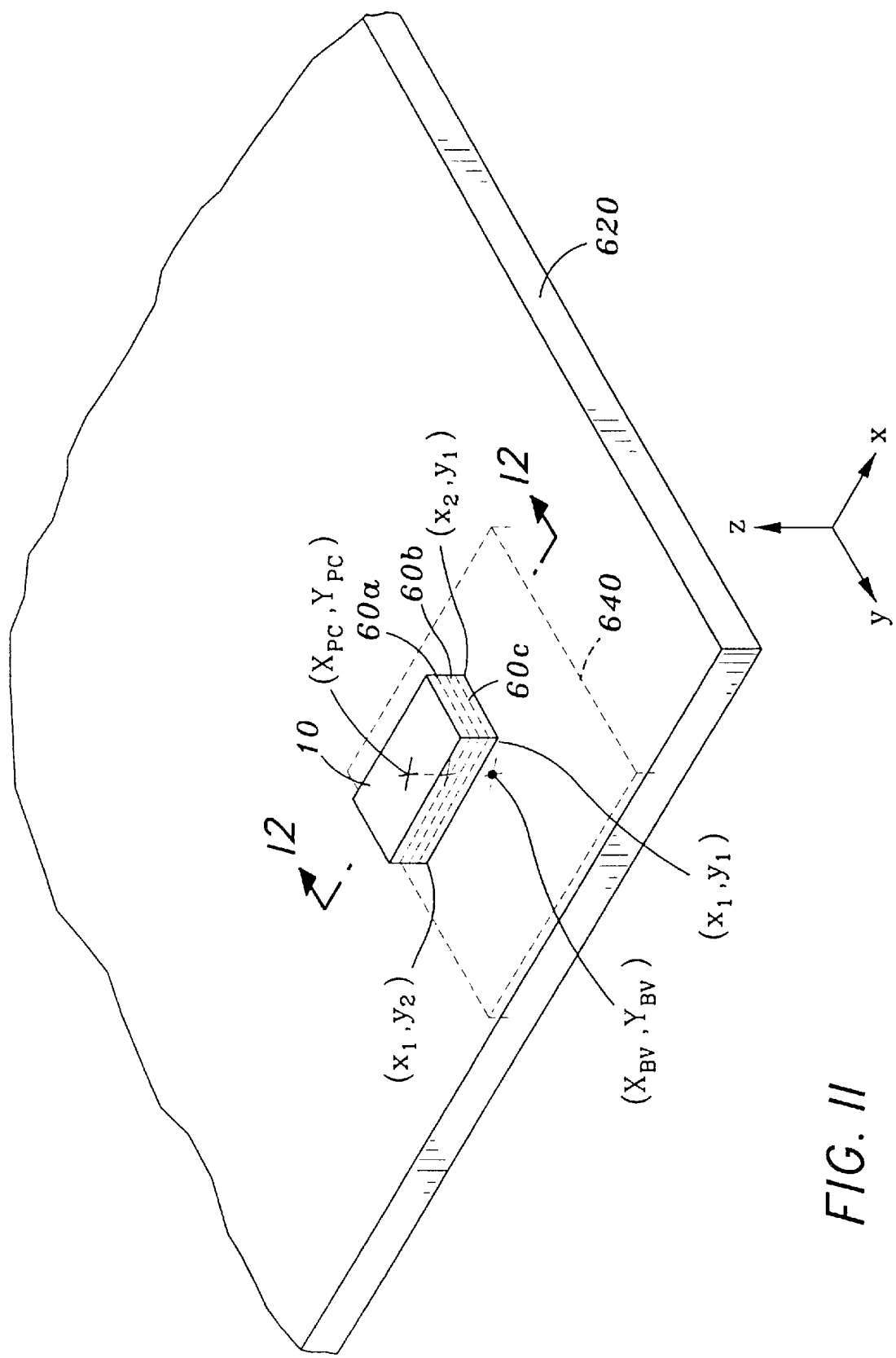
FIG. 11 shows a perspective view of the test object 10 shown in FIG. 2a mounted on a circuit board.
Figure 12:
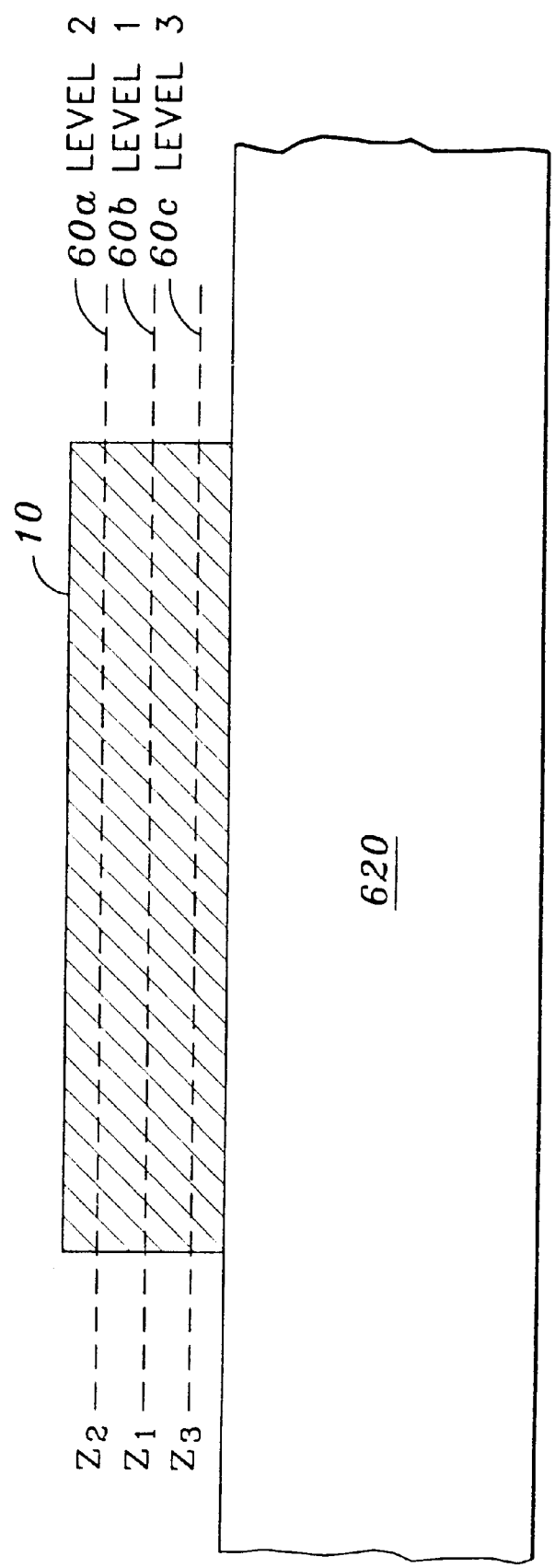
FIG. 12 shows a cross sectional view of the test object 10 mounted on the circuit board shown in FIG. 11.

A specific example, shown in FIGS. 11, 12, 13 and 14, is used in the following discussion to illustrate the application of on-the-fly CAD data modification for analysis of laminographic circuit board images using the FOVCorrection conversion factor, location conversion factors, and length conversion factors. FIGS. 11 and 12 show a perspective view and a cross sectional view, respectively, of the test object 10 (see FIG. 2a) mounted on a circuit board 620. Three corners of the test object 10 are located at circuit board coordinates $(x_1,y_1,),(x_2,y_1,)$ and $(x_1,y_2)$. The center of the test object 10 is located at circuit board coordinates $(x_{Pc},y_{Pc})$. Referring to FIGS. 10 and 12, the circle image plane 60b in the test object 10 is located at the distance $z_1$ from the plane 64 of the X-ray detector 30 (Level 1); the arrow image plane 60a in the test object 10 is located at the distance $z_2$ from the plane 64 of the X-ray, detector 30 (Level 2); and the cross image plane 60c in the test object 10 is located at the distance $z_3$ from the plane 64 of the X-ray detector 30 (Level 3). As shown in FIG. 11, coordinates $(x_{BV},y_{BV})$ identify a first board view location on circuit board 620.

For purposes of this example, the test object 10 has been selected to have the following physical characteristics: a length of approximately 413 mils; a width of approximately 213 mils; a height of approximately 240 mils; the circle image plane 60b (Level 1) positioned in the middle of the height dimension; the arrow image plane 60a (Level 2) positioned 60 mils above Level 1; and the cross image plane 60c (Level 3) positioned 60 mils below Level 1. Additionally, the laminography system selected for the inspection of the test object 10 having these physical characteristics is the specific example system summarized in Table 2.

As previously stated, it is often more efficient to store the design CAD data for a particular circuit board in pixel format. In one implementation of the present invention, it has been found that on-the-fly calculation times can be minimized if the CAD data is stored in the analysis system in a pixel format which corresponds to a specific nominal/reference FOV. Additionally, inspection procedures may be defined for each particular circuit board. These inspection procedures include defining specific board views and objects or features (e.g., solder joints) to inspect in each board view.

For example, one inspection procedure designed to check the position and dimensions of the test object 10 on circuit board 620 and the features of the circle 82, arrow 81 and cross 83 in the test object 10 at Levels 1, 2 and 3, respectively, includes the following steps. First, determine a first board view location at board coordinates $(x_{B_v},y_{B_v})$ such that Level 1, 2 and 3 board views at this location include the test object 10. Second, define a first board view centered at board coordinates $(x_{B_v},y_{B_v})$ at the first Z-axis level $z_1$, (Level 1) and select the FOV of the first board view as the nominal FOV. Third, define a second board view centered at board coordinates $(x_{BV},y_{BV})$ at the second Z-axis level $z_2$ (Level 2) and select the FOV of the second board view as the first current FOV. Fourth, define a third board view centered at board coordinates $(x_{BV},y_{Bv})$ at the third Z-axis level $z_3$ (Level 3) and select the FOV of the third board view as the second current FOV.

Implementation of this procedure to check the position and dimensions of the test object 10 on circuit board 620 and the features of the circle 82, arrow 81 and cross 83 in the test object 10 at Levels 1, 2 and 3, respectively, includes creating a pixel format CAD database which describes the features of the test object 10 from the physical dimensions CAD database for the test object 10. An example of a pixel format CAD database 720cd corresponding to the first board view centered at board coordinates $(x_{BV},y_{BV})$ at the first Z-axis level $z_1$, (Level 1) and the nominal FOV is shown in FIG. 13A. The CAD data 720cd for Level 1 shows the center of the first board view, corresponding to the first board view dimensional coordinates $(x_{BV},y_{BV})$, located at pixel coordinates 0 024,1024). Additionally, the CAD data 720cd for Level 1 shows:

a) the three corners of the test object 10 corresponding to the dimensional coordinates $(x_1,y_2),(x_1,y_1)$ and $(x_2,y_1)$, located at pixel coordinates (195,920), 0 253,920) and (1253,375), respectively; and b) the center of the test object corresponding to the dimensional coordinates $(x_{PC},y_{PC})$, located at pixel coordinates (724,648).

Figure 14B:
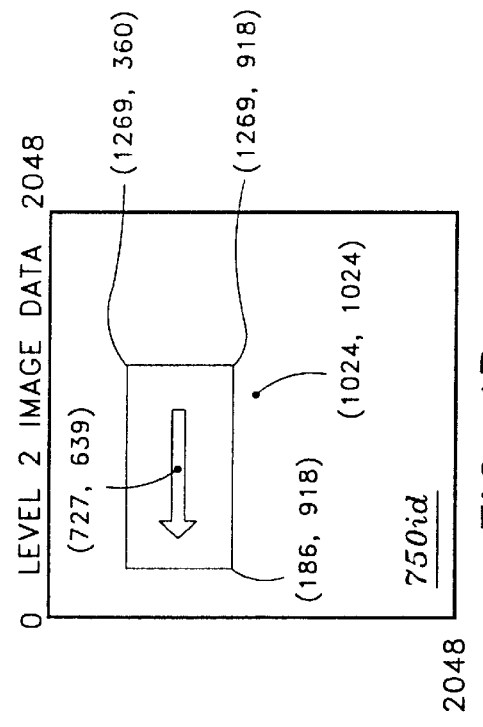
FIGS. 14A, 14B, and 14C show laminographic images of the test object 10 shown in FIGS. 2, 11 and 12 corresponding to the CAD data in FIGS. 13A, 13B and 13C.
Figure 14A:
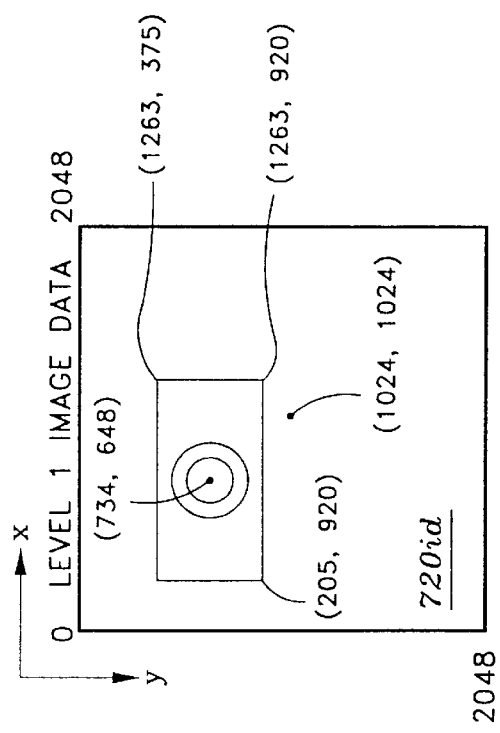

A first laminographic image or board view 720id corresponding to the first board view location $(x_{BV},y_{BV})$ at the first Z-axis level $z_1$ (Level 1) of test object 10 is shown in FIG. 14A. The image data 720id for Level 1 shows the center of the first board view, corresponding to the first board view dimensional coordinates $(x_{BV},y_{BV})$, located at image pixel coordinates (1024,1024). The field of view (FOV) of the first board view image data 720id at Level 1, i.e., the portion of the circuit board 620 at the first Z-axis level $z_1$, centered at the first board view location $(x_{BV},y_{BV})$ which is included in the first laminographic board view image 720id, is represented by the dashed line perimeter 640 in FIG. 11.

In this example, the FOV 640 at the dashed line position is selected as the "nominal FOV and has a size of approximately 800 mils×800 mils (see Table 10).

In a typical circuit board inspection system according to the present invention, the CAD data which describes features in the first field of view 640 (e.g., the location and dimensions of the test object 10, the circles within the plane 60b of the test object 10, etc.) are available to the analysis portion of the inspection system in pixel format. As shown in the first board view image data 720id in FIG. 14A: a) the test object 10 forms an image having corners at pixel locations (205,920), (1263,920) and (1263,375) corresponding to the corners $(x_1,y_2),(x_1,y_1)$ and $x_2,y_1$), respectively, of the test object 10; and b) the center of the test object 10 forms an image at pixel locations (734,648) corresponding to the center $(x_{PC},y_{PC})$ of the test object 10. Since the FOV 640 was selected as the "nominal FOV", the first board view image data at level $z_1$, 720id (FIG. 14A) may be compared directly to the pixel format test object 10 CAD data at level $z_1$, (FIG. 13A) corresponding to the first board view centered at board coordinates $(x_{B_v},y_{B_v})$ at the first Z-axis level $z_1$. This comparison of the image data 720id (FIG. 14A) with the corresponding CAD data 720cd (FIG. 13A) reveals that the test object 10 is shifted in the positive x direction by 10 pixels and is positioned correctly in the y direction.

Figure 14C:
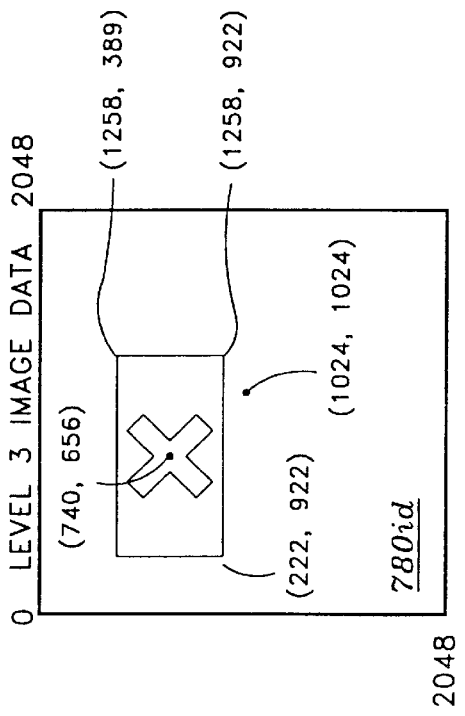

In accordance with the present invention, inspection of the arrow image plane 60a (Level 2 at $z_2$) positioned 60 mils above Level 1; and the cross image plane 60c (Level 3 at $z_3$) positioned 60 mils below Level 1, is accomplished by changing the radius of the X-ray source as summarized in Table 2. Thus, to change from Level 1 to Level 2, the radius of the X-ray source is changed from approximately 1.55 inches to approximately 1.50 inches which also changes the FOV from approximately 800 mils×800 mils to approximately 780 mils×780 mils. A second laminographic image or board view 750id corresponding to the first board view location $(x_{B_v},y_{B_v})$ at the second Z-axis level $z_2$ (Level 2) of test object 10 is shown in FIG. 14B. The image data 750id for Level 2 shows the center of the first board view, corresponding to the first board view dimensional coordinates $(x_{BV},y_{BV})$, located at image pixel coordinates (1024, 1024). The field of view (FOV) of the first board view image data 750id at Level 2, i.e., the portion of the circuit board 620 at the second Z-axis level $z_2$ centered at the first board view location $(x_{BV}, y_{BV})$ which is included in the second laminographic board view image 750id, is selected as the first "current FOV" and has a size of approximately 780 mils×780 mils (see Table 2). Similarly, to change from Level 1 to Level 3, the radius of the X-ray source is changed from approximately 1.55 inches to approximately 1.59 inches which also changes the FOV from approximately 800 mils× 800 mils to approximately 820 mils×820 mils. A third laminographic image or board view 780id corresponding to the first board view location $(x_{BV}, y_{BV})$ at the third Z-axis level $z_3$ (Level 3) of test object 10 is shown in FIG. 14C. The image data 780id for Level 3 shows the center of the first board view, corresponding to the first board view dimensional coordinates $(x_{BV}, y_{BV})$, located at image pixel coordinates (1024,1024). The field of view (FOV) of the first board view image data 780id at Level 3, i.e., the portion of the circuit board 620 at the third Z-axis level $z_3$ centered at the first board view location $(x_{BV}, y_{BV})$ which is included in the third laminographic board view image 780id, is selected as the second "current FOV" and has a size of approximately 820 mils×820 mils (see Table 2).

The FOV Correction factor previously defined in equation 11, is used to perform the on-the-fly conversion of specific X,Y coordinates in the CAD data from a NominalFOV to a CurrentFOV as follows:

CurrentX=(NominalX−ImageCenterX)*FOVCorrection+ImageCenterX

CurrentY=(NominalY−ImageCenterY)*FOVCorrection+ImageCenterY (12)

The FOVCorrection factor is also used to perform on-the-fly conversion of specific dimensions in the X-axis and Y-axis directions, ΔX and ΔY, in the CAD data from a NominalFOV to a CurrentFOV as follows:

CurrentΔX=NominalΔX*FOVCorrection

CurrentΔY=NominalΔY*FOVCorrection (13)

Figure 13B:
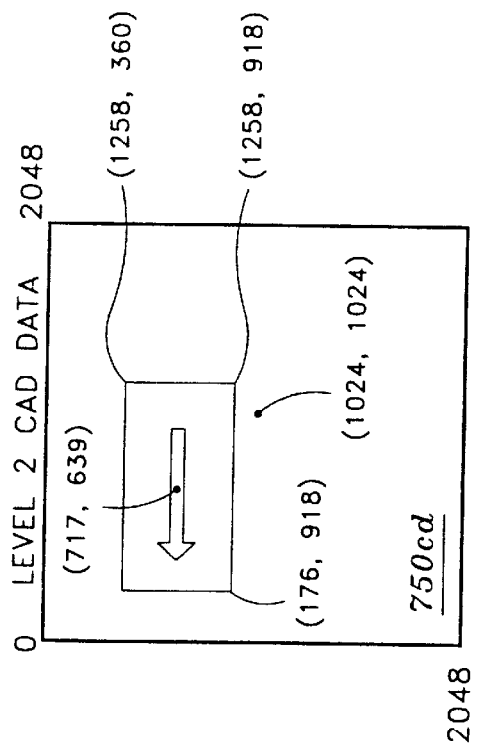
FIGS. 13A, 13B, and 13C show CAD data for the test object 10 shown in FIGS. 2, 11 and 12.
Figure 13A:
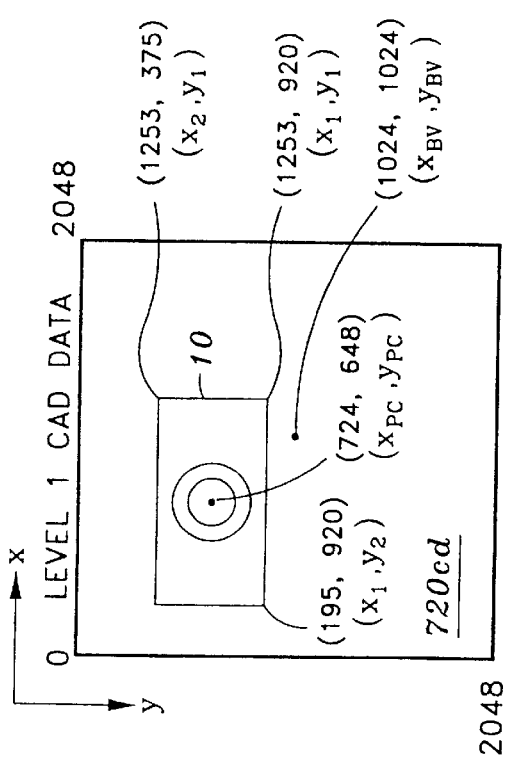
Figure 13C:
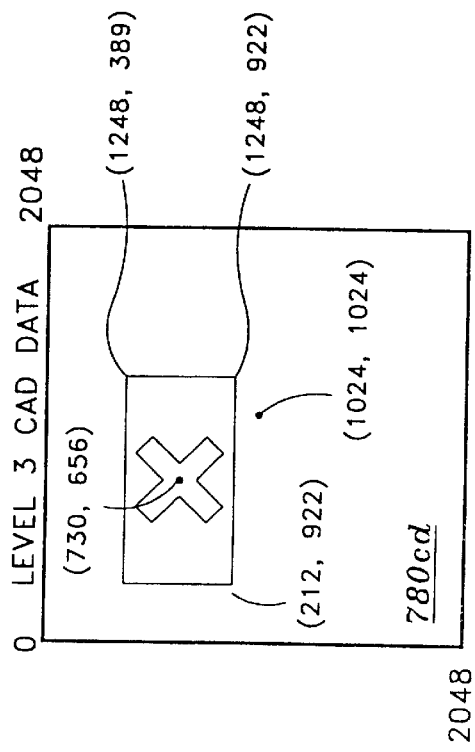

Examples of on-the-fly conversion of the nominal FOV CAD database 720cd for test object 10 at Level 1 shown in FIG. 13A to the first current view at Level 2 and the second current view at Level 3 are shown in FIGS. 13B and 13C, respectively. For example, equations 12 convert the CAD data of Level 2 at the nominal FOV of Level 1 to the first current FOV of Level 2 (FIG. 13B) as follows: a) the three corners of the test object 10 corresponding to the dimensional coordinates $(x_1,y_2)$, $(x_1,y_1)$ and $(x_2,y_1)$, are located at pixel coordinates (176,918), (1258,918) and (1258,360), respectively, in the first current FOV; and b) the center of the test object 10 corresponding to the dimensional coordinates $(x_{PC}, y_{PC})$, is located at pixel coordinates (717,639) in the first current FOV. Similarly, equations 12 convert the CAD data of Level 3 at the nominal FOV of level 1 to the second current FOV of Level 3 (FIG. 13C) as follows: a) the three corners of the test object 10 corresponding to the dimensional coordinates $(x_1,y_2)$, $(x_1,y_1)$ and $(x_2,y_1)$, are located at pixel coordinates (212,922), (1248,922) and (1248,389), respectively, in the second current FOV; and b) the center of the test object 10 corresponding to the dimensional coordinates $(x_{PC}, y_{PC})$, is located at pixel coordinates (730,656) in the second current FOV. Thus, analysis of the laminographic image for Level 2 (FIG. 14B) is accomplished using the first current FOV on-the-fly converted CAD data for Level 2 (FIG. 13B) and analysis of the laminographic image for Level 3 (FIG. 14C) is accomplished using the second current FOV on-the-fly converted CAD data for Level 3 (FIG. 13C). Equations 13 are employed in a similar manner to convert lengths in the CAD data of Level 1 (FIG. 13A) at the nominal FOV to the first current FOV of Level 2 (FIG. 13B) and the second current FOV of Level 3 (FIG. 13C) for comparison to the corresponding laminographic images at Levels 1, 2 and 3.

Examples of specific parameters which are often used for inspection of solder joints/electrical connections include pad locations, pin locations, and pad dimensions. On-the-fly conversion of the CAD fields/data for these parameters may be accomplished as follows:

PadXLocation=(NominalPadX−XImageCenter)*FOVCorrection+XImageCenter

PadYLocation=(NominalPadY−YImageCenter)*FOVCorrection+YImageCenter (14)

PinXLocation=(NominalPinX−XImageCenter)*FOVCorrection+XImageCenter

PinYLocation=(NominalPinY−YImageCenter)*FOVCorrection+YImageCenter (15)

PadDx=NominalPadDx*FOVCorrection

PadDy=NominalPadDy*FOVCorrection

PinDx=NominalPinDx*FOVCorrection

PinDy=NominalPinDY*FOVCorrection (16)

These coordinate translations and scaling are performed for each slice of each board view for each board inspected, based on the current Z height which determines the current FOV and magnification.

As presented in the above discussion and specific examples, the coordinates of features on the circuit board are referenced to the selected board view. Thus, the same features, referenced to a different board view would have different coordinates. Many such issues arise in the specific application of the present invention and do not limit the scope of the present invention, as its teachings can be readily adapted to numerous analysis conventions.

Figure 15:
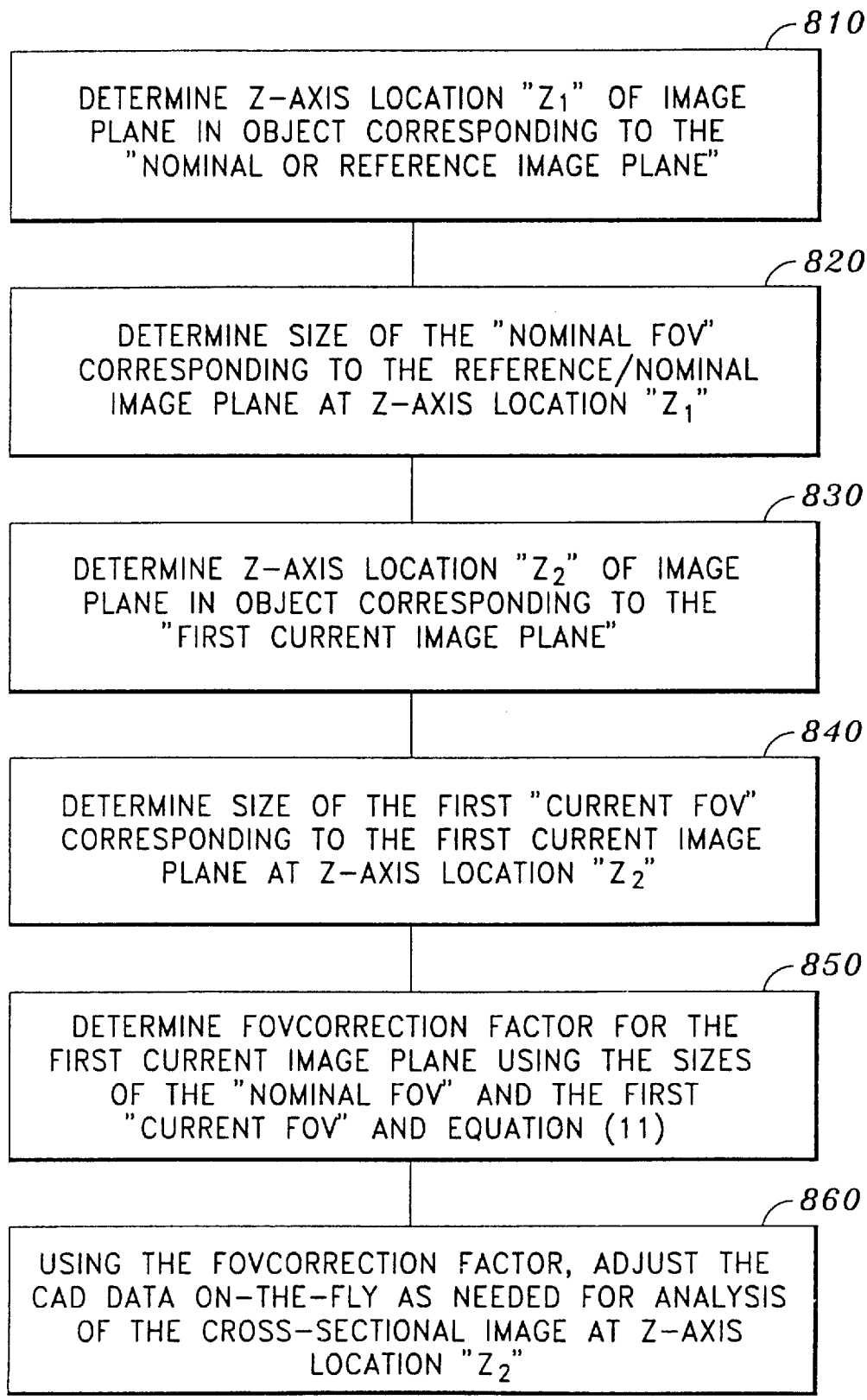
FIG. 15 is a flow chart showing a process for performing on-the-fly CAD data manipulations for the analysis of laminographic images.

The process for performing on-the-fly CAD data manipulations for the analysis of laminographic images according to the present invention is summarized in the flow chart shown in FIG. 15. In block 810, a "Nominal or Reference Image Plane" at a Z-axis location "$z_1$," in the object being inspected is determined. In block 820, the size of the "Nominal FOV" corresponding to the Reference/Nominal Image Plane at Z-axis location "$z_1$" is determined. In block 830, a "First Current Image Plane" at a Z-axis location "$z_s$" in the object being inspected is determined. In block 840, the size of the First "Current FOV" corresponding to the First Current Image Plane at Z-axis location "$z_2$" is determined. In block 850, an FOVCorrection Factor for the First Current Image Plane is determined by using the sizes of the "Nominal FOV"; the First "Current FOV" and Equation (11). In block 860, the FOVCorrection Factor is used to adjust the CAD data on-the-fly as needed for the analysis of the cross-sectional laminographic image at Z-axis location "$z_2$". While the above discussion has been in terms of an FOV-Correction factor based on relative sizes of the fields of view at different Z-axis locations, a similar and equivalent procedure could also be performed using other parameters, for example, the magnification factors for the different Z-axis locations. These and other such modifications are considered to be included within the scope of the present invention.

Other Issues and Considerations

Since the present system supplies cross-sectional images at various Z heights, a common use is to take multiple slices of a solder joint and correlate data between slices. Although the distances between slices are generally small, a few mils, for most surface mount devices, more substantial distances can be encountered for certain specific device types. For example, BGA devices are sometimes imaged at both the top and bottom of the ball, which is a distance of approximately 25 mils. Plated Through Hole (PTH) devices are imaged on both the top and bottom pads, which will be the entire board thickness, which is a distance of approximately 70 mils. For these larger distances, some measurements must be corrected.

For example, a locator algorithm is usually run at the center of the ball for BGA devices. The x and y coordinates it finds will correspond to different x and y locations on different slices, such as the pad slice and the top package slice.

Similarly a PTH location found in the barrel may need to be adjusted on the top and bottom pad. These can be cleverly handled by correcting these locations in a software module, which maintains and distributes these located positions to the algorithms. Similar magnification corrections to those discussed above to correct CAD locations can be applied to the locator positions at runtime as well.

Similarly, size measurement may need normalization depending on the Z-height of the slice used to gather the measurement. For example, any measurements in units of pixel distances, if they exist, must be converted to mils using the current perturbed FOV before any comparison or use on different slices.

Summary, Ramifications and Scope

Accordingly, the reader will see that the present invention solves many of the specific problems encountered when inspecting solder connections on circuit boards. Particularly important is that it removes the need for a mechanical means to move the circuit board along the Z-axis without impeding the analysis of the laminographic images at various Z-axis levels in the circuit board. Furthermore, the electronic relocation of the image plane with respect to the inspection system coupled with on-the-fly CAD data modification provides a processor time and data storage resource efficient means for acquiring images at the desired Z levels of the circuit board and analyzing these images by recalling, modifying and applying the CAD data for use on an as needed basis.

Although the description above contains many specificities, these should not be construed as limiting the scope of the invention but as merely providing illustrations of some of the presently preferred embodiments of this invention. For example, alternative techniques and image parameters may be used to determine how to convert the CAD data for use at the nominal FOV for use at a current FOV. Additionally, alternative CAD data parameters may be used for image analysis; alternative techniques may be used to acquire the cross sectional images; alternative methods may be used for changing the Z-axis level at which images are acquired; etc.

The invention may be embodied in other specific forms without departing from its spirit or essential characteristics. The described embodiments are to be considered in all respects only as illustrative and not restrictive. The scope of the invention is, therefore, indicated by the appended claims and their legal equivalents, rather than by the foregoing description and specific examples given. All changes which come within the meaning and range of equivalency of the claims are to be embraced within their scope.

Therefore, having thus described the invention, at least the following is claimed:

1. A processor configured to control the acquisition and analysis of cross-sectional images of an object in an x-ray inspection system, each cross-sectional image corresponding to a Z-axis position, the processor programmed to perform the steps of:
   receiving a current Z-axis position of a current cross-section of an object to be inspected, the current Z-axis position defining a Z-axis variance relative to a reference Z-axis position of a reference cross-section of the object;
   based on the Z-axis variance, generating a current cross-sectional image of the object at the current Z-axis position; and
   based on the Z-axis variance, modifying design data that models the reference cross-section of the object.

2. The processor of claim 1, wherein the processor is further programmed to perform the step of comparing the current cross-sectional image of the object to the modified design data.

3. The processor of claim 1, wherein the step of modifying the design data based on the Z-axis variance further comprises converting the design data into a pixel coordinate format.

4. The processor of claim 1, wherein the object being inspected comprises a printed circuit board.

5. The processor of claim 1, wherein the step of modifying the design data based on the Z-axis variance comprises manipulating the design data on-the-fly.

6. The processor of claim 1, wherein the step of generating a current cross-sectional image of the object further comprises determining a current field of view (FOV) based on the Z-axis variance.

7. The processor of claim 1, wherein the step of generating a current cross-sectional image of the object further comprises determining a current magnification factor based on the Z-axis variance.

8. The processor of claim 6, wherein the step of modifying the design data further comprises modifying the design data based on a comparison between the current FOV and a reference FOV associated with the reference Z-axis position.

9. The processor of claim 7, wherein the step of modifying the design data further comprises modifying the design data based on a comparison between the current magnification factor and a reference magnification factor associated with the reference Z-axis position.

10. An x-ray inspection system for acquiring and analyzing cross-sectional images of an object, the x-ray inspection system comprising:
    a source of x-rays configured to emit x-rays through an object to be inspected;
    an x-ray detector system configured to receive the x-rays produced by the source of x-rays and generate a cross-sectional image of a portion of the object being;
    logic configured to receive a current Z-axis position of a current cross-section of an object to be inspected, the current Z-axis position defining a Z-axis variance relative to a reference Z-axis position of a reference cross-section of the object;
    logic configured to generate, based on the Z-axis variance, a current cross-sectional image of the object at the current Z-axis position; and logic configured to modify, based on the Z-axis variance, design data that models the reference cross-section of the object.

11. The x-ray inspection system of claim 10, further comprising logic configured to compare the current cross-sectional image of the object to the modified design data.

12. The x-ray inspection system of claim 10, wherein the logic configured to modify the design data based on the Z-axis variance further comprises logic configured to convert the design data into a pixel coordinate format.

13. The x-ray inspection system of claim 10, wherein the object being inspected comprises a printed circuit board.

14. The x-ray inspection system of claim 10, wherein the logic configured to modify the design data based on the Z-axis variance further comprises logic configured to manipulate the design data on-the-fly.

15. The x-ray inspection system of claim 1, wherein the logic configured to generate a current cross-sectional image of the object further comprises logic configured to determine a current field of view (FOV) based on the Z-axis variance.

16. The x-ray inspection system of claim 10, wherein the logic configured to generate a current cross-sectional image of the object further comprises logic configured to determine a current magnification factor based on the Z-axis variance.

17. The x-ray inspection system of claim 15, wherein the logic configured to modify the design data further comprises logic configured to modify the design data based on a comparison between the current FOV and a reference FOV associated with the reference Z-axis position.

18. The x-ray inspection system of claim 16, wherein the logic configured to modify the design data further comprises logic configured to modify the design data based on a comparison between the current magnification factor and a reference magnification factor associated with the reference Z-axis position.

19. The x-ray inspection system of claim 10, wherein the logic comprises software residing in memory and further comprising a processor configured to implement the logic.

20. A method for acquiring and analyzing cross-sectional images in an x-ray inspection system, the method comprising the steps of:

receiving a current Z-axis position of a current cross-section of an object to be inspected, the current Z-axis position defining a Z-axis variance relative to a reference Z-axis position of a reference cross-section of the object;

based on the Z-axis variance, generating a current cross-sectional image of the object at the current Z-axis position; and based on the Z-axis variance, modifying design data that models the reference cross-section of the object.

21. The method of claim 20, further comprising the step of comparing the current cross-sectional image of the object to the modified design data.

22. The method of claim 20, wherein the step of modifying the design data based on the Z-axis variance further comprises converting the design data into a pixel coordinate format.

23. The method of claim 20, wherein the object being inspected comprises a printed circuit board.

24. The method of claim 20, wherein the step of modifying the design data based on the Z-axis variance comprises manipulating the design data on-the-fly.

25. The method of claim 20, wherein the step of generating a current cross-sectional image of the object further comprises determining a current field of view (FOV) based on the Z-axis variance.

26. The method of claim 20, wherein the step of generating a current cross-sectional image of the object further comprises determining a current magnification factor based on the Z-axis variance.

27. The method of claim 25, wherein the step of modifying the design data further comprises modifying the design data based on a comparison between the current FOV and a reference FOV associated with the reference Z-axis position.

28. The method of claim 26, wherein the step of modifying the design data further comprises modifying the design data based on a comparison between the current magnification factor and a reference magnification factor associated with the reference Z-axis position.

29. A system for acquiring and analyzing cross-sectional images of an object in an x-ray inspection system, system comprising:

a means for receiving a current Z-axis position of a current cross-section of an object to be inspected, the current Z-axis position defining a Z-axis variance relative to a reference Z-axis position of a reference cross-section of the object;

a means for generating, based on the Z-axis variance, a current cross-sectional image of the object at the current Z-axis position by emitting x-rays through the current cross-section of the object and generating a corresponding x-ray image; and a means for modifying, based on the Z-axis variance, design data that models the reference cross-section of the object.

30. The system of claim 29, further comprising a means for comparing the current cross-sectional image of the object to the modified design data.

* * * * *